US010286015B2

(12) United States Patent
Sing et al.

(10) Patent No.: US 10,286,015 B2
(45) Date of Patent: *May 14, 2019

(54) METHODS FOR TREATING TRAUMATIC BRAIN INJURY WITH AMNION-DERIVED CELLULAR CYTOKINE SOLUTION (ACCS) OR AMNION-DERIVED MULTIPOTENT PROGENITOR (AMP) CELLS

(71) Applicant: Noveome Biotherapeutics, Inc., Pittsburgh, PA (US)

(72) Inventors: George L Sing, New York, NY (US); Vivienne S Marshall, San Antonio, TX (US)

(73) Assignee: Noveome Biotherapeutics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,133

(22) Filed: Apr. 25, 2017

(65) Prior Publication Data

US 2017/0224740 A1   Aug. 10, 2017

Related U.S. Application Data

(60) Continuation of application No. 14/028,935, filed on Sep. 17, 2013, now abandoned, which is a continuation of application No. 13/478,697, filed on May 23, 2012, now abandoned, which is a division of application No. 12/152,207, filed on May 13, 2008, now Pat. No. 8,197,804, which is a continuation-in-part of application No. PCT/US2008/004583, filed on Apr. 9, 2008.

(60) Provisional application No. 60/928,801, filed on May 11, 2007, provisional application No. 60/923,436, filed on Apr. 13, 2007.

(51) Int. Cl.
| | |
|---|---|
| A61K 35/12 | (2015.01) |
| A61K 35/48 | (2015.01) |
| A61K 35/50 | (2015.01) |
| A61K 38/17 | (2006.01) |
| A61K 45/06 | (2006.01) |
| A61L 27/38 | (2006.01) |
| A61K 38/18 | (2006.01) |
| A61K 38/19 | (2006.01) |
| A61K 38/22 | (2006.01) |
| A61K 38/30 | (2006.01) |
| C12N 5/073 | (2010.01) |

(52) U.S. Cl.
CPC .............. *A61K 35/50* (2013.01); *A61K 35/48* (2013.01); *A61K 38/177* (2013.01); *A61K 38/179* (2013.01); *A61K 38/18* (2013.01); *A61K 38/185* (2013.01); *A61K 38/1808* (2013.01); *A61K 38/1825* (2013.01); *A61K 38/19* (2013.01); *A61K 38/193* (2013.01); *A61K 38/2292* (2013.01); *A61K 38/30* (2013.01); *A61K 45/06* (2013.01); *A61L 27/3804* (2013.01); *A61L 27/3878* (2013.01); *C12N 5/0605* (2013.01); *A61K 35/12* (2013.01); *C12N 2533/54* (2013.01); *Y02A 50/465* (2018.01)

(58) Field of Classification Search
None
See application file for complete search history.

(56) References Cited

U.S. PATENT DOCUMENTS

| | | |
|---|---|---|
| 2003/0087394 A1 | 5/2003 | Sharma et al. |
| 2004/0161419 A1 | 8/2004 | Strom et al. |
| 2005/0019865 A1 | 1/2005 | Kihm et al. |
| 2005/0032209 A1 | 2/2005 | Messina et al. |
| 2005/0054098 A1 | 3/2005 | Mistry et al. |
| 2005/0058629 A1 | 3/2005 | Harmon et al. |
| 2005/0152995 A1 | 7/2005 | Chen et al. |
| 2006/0030039 A1 | 2/2006 | Chen et al. |
| 2006/0078543 A1 | 4/2006 | Reubinoff et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0188983 A1 | 8/2006 | Harris et al. |
| 2006/0222634 A1 | 10/2006 | Clarke et al. |

(Continued)

FOREIGN PATENT DOCUMENTS

| | | |
|---|---|---|
| WO | WO200073421 | 12/2000 |
| WO | WO2006105152 | 10/2006 |

OTHER PUBLICATIONS

Zohar et al., Neuroscience, 2003; 118: 949-955 (Year: 2003).*
Van Stavern et al., J Neuroophthalmol. 2001; 21: 112-117 (Year: 2001).*
Liu et al., Journal of the Neurological Sciences, 2001; 187: 91-97 (Year: 2001).*

(Continued)

*Primary Examiner* — Christina M Borgeest
(74) *Attorney, Agent, or Firm* — Linda O. Palladino; Gail N. Kempler

(57) ABSTRACT

The invention is directed to methods for treating nervous system injury and disease, in particular traumatic brain injury and degenerative nervous system disease. Such methods utilize novel compositions, including but not limited to trophic factor-secreting extraembryonic cells (herein referred to as TSE cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents.

6 Claims, No Drawings

(56) References Cited

U.S. PATENT DOCUMENTS

| | | | |
|---|---|---|---|
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009492 A1 | 1/2007 | Shi et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |

OTHER PUBLICATIONS

The website: https://www.brainandspinalcord.org/closed-head-injury/, downloaded on Mar. 16, 2019; 3 pages total (Year: 2019).*
Clarke, D., et al, Curr Opin Gen Dev 2001, 11:575-580.
Horner, P., et al., Nature 2000, 407(26):963-970.
Sheng, J.G., et al., Exp Neurol 1993, 123:192-203.
Steed, D.L., et al, ePlasty 2008, 8:e18.
Miki, T., et al., Stem Cell Reviews, 2006, 2:133-141.
Parolini, O., et al., Stem Cells, 2008, 26:300-311.
Kakishita, K., et al., Brain Research 2003, 980:48-56.
Cao, Q., et al., J Neurosci Res 2002, 68:501-510.
Anderson, A.J., et al., J Neurotrauma 2004, 21(12):1831-1846.
Meng, X., et al., Bell Bio Int'l, 2007, 31:691-698.
Okawa, H., et al., NeuroReport 2002, 12(18):4003-4007.
Kakishita, K., et al., Exp Neurol 2000, 165:27-34.
Lindvall, O., et al., Nature 2006, 41:1094-1096.
Cummings, B., et al., Neurol Res 2006, 28474-481.
Pallini, R., et al., Neurosurg 2005, 57(5):1014-1025.
Sankar, V., et al., Neurosci 2003, 118:11-17.
Wu, Z., et al., Chinese Med J 2006, 119(24):2101-2107.
Uchida, S., et al., J Neurosci Res 2000, 62:585-590.
Heeger, P., Transplantation 2004, 78(10):1411-1412.
Bailo, M., et al., Transplantation 2004, 78(10):1439-1448.
Rodgerson, D., et al., Life Extension 2007, 41-48.
Chen, Z., et al., J Neurotrauma 2009, 26(11):1987-1997.

* cited by examiner

METHODS FOR TREATING TRAUMATIC BRAIN INJURY WITH AMNION-DERIVED CELLULAR CYTOKINE SOLUTION (ACCS) OR AMNION-DERIVED MULTIPOTENT PROGENITOR (AMP) CELLS

CROSS-REFERENCE TO RELATED APPLICATIONS

This application claims priority under 35 USC § 119(e) of U.S. Provisional Application Nos. 60/923,436, filed Apr. 13, 2007; 60/928,801, filed May 11, 2007; and 60/930,845, filed May 18, 2007; and is a continuation-in-part application claiming priority under 35 USC § 365(c) to International Application No. PCT/US2008/04583, filed Apr. 9, 2008, the entireties of which are incorporated herein by reference.

FIELD OF THE INVENTION

The field of the invention is directed to methods for treating nervous system injury and disease, in particular traumatic brain injury and degenerative nervous system disease. Such methods utilize novel compositions, including but not limited to trophic factor-secreting extraembryonic cells (herein referred to as TSE cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents.

DESCRIPTION OF RELATED ART

Williams, A. J. et al, (Neuroscience Letters (2006), pp. 183-188) report that severity level and injury track determine outcome following penetrating ballistic-like brain (PBBI) injury in the rat. Williams, A. J., et al, (J Neurotrauma (2006) 23(12):1828-1846), studied acute and delayed cerebral injury in a rat model of PBBI and found that differential time courses for hemorrhage, cell death, inflammation and remote degeneration exist in this type of brain injury. Schouten J W, et al. (2004) J Neurotrauma 21:1501-1538, present a review and rationale for the use of cellular transplantation as a therapeutic strategy for traumatic brain injury. Rice A C, et al, (2003) Exp Neurol 183 (2):406-417, describe proliferation and neuronal differentiation of mitotically active cells following traumatic brain injury. Gantwerker B D, et al., (2007) Barrow Quarterly 23(1):1517, discuss current concepts in neural regeneration after traumatic brain injury.

Clarke D, Frizen J. (2001) Curr Opin Genet Dev 11:575-580, describe the differentiation potential of adult stem cells. Homer P G, Gage F H. (2000) Nature 407:963-970, describe regenerating damaged central nervous system tissue.

Cao Q, et al, (2002) J Neurosci Res 68:501-510, describe stem cell repair of central nervous system injury. Bambakitis N C, et al., (2005) Neurosurg Focus in Medscape 19(3):1-9, describe endogenous stem cell proliferation after central nervous system injury: alternative therapeutic options.

Uchida S, et al. (2000) J Neurosci Res 62:585-590, describe the neurotrophic function of conditioned medium from human amniotic epithelial cells. Sheng, J G., et al. (1993) Exp Neurol 123(2):192-203, report on dopaminergic sprouting and behavioral recovery in hemi-parkinsonian rats after implantation of amnion cells. Lindvall, O. and Kokaia, Z., (2006) Nature 441:1094-1096, describe progress in the use of stem cells for the treatment of neurological disorders. Kakishita, K., et al., (2000) Exp Neurol 165:27-34, report that human amniotic epithelial cells produce dopamine and survive after implantation into the striatum of a rat model of Parkinson's disease. Okawa, H., et al., (2001) Neuroreport 12(18):4003-7, report that amniotic epithelial cells transform into neuron-like cells in the ischemic brain. Kakishita, K., et al., (2003) Brain Res 980(1):48-56 describe implantation of human amniotic epithelial cells prevents the degeneration of nigral dopamine neurons in rats with 6-hydroxy-dopamine lesions. Meng, X T, et al., (2007) Cell Biol Int 31(7):691-8, report enhanced neural differentiation of neural stem cells and neurite growth by amniotic epithelial cell co-culture.

Sankar, V. et al., (Neuroscience 2003, Letter to Neuroscience, 118(1):11-7) studied the role of human amniotic epithelial cell transplantation in transected spinal cord injury repair and reported that the human amniotic epithelial cells survived in monkey transected spinal cord, the graft was penetrated by host axons and there was no glial scar at the transection lesion site. Wu, Z-Y., et al, (Chinese Med Jour 2006, 119(24):2101-07) reported that transplantation of human amniotic epithelial cells improves hindlimb function in rats with spinal cord injury.

BACKGROUND OF THE INVENTION

The term "nervous system injury" refers to any injury of the nervous tissue and can be caused by fracture or penetration of the skull or vertebra (such as in the case of a vehicle accident, fall or gunshot wound resulting in damage to the brain or spinal cord), a disease process (neurotoxins, infections, tumors, metabolic abnormalities, genetic abnormalities, degenerative nerve diseases, etc.), a closed head injury such as rapid acceleration or deceleration of the head (i.e. Shaken Baby Syndrome) causing injury to the brain, or an injury or disease affecting the peripheral nerves. Such injuries can have devastating lifelong effects on physical and mental functioning.

Traumatic Brain Injury (TBI)

There are many complications associated with brain injury. For example, ~25% of patients with brain contusions or hematomas and ~50% of patients with penetrating head injuries will develop immediate seizures that occur within the first 24 hours of the injury. These immediate seizures increase the risk of early seizures which are defined as seizures occurring within one week after injury. However, these seizures do not seem to be linked to the development of post-traumatic epilepsy (recurrent seizures occurring >1 week after initial trauma).

Another complication of brain injury is hydrocephalus or post-traumatic ventricular enlargement. This complication occurs when cerebrospinal fluid (CSF) accumulates in the brain resulting in dilation of the cerebral ventricles and an increase in intracranial pressure (ICP). This condition can develop during the acute stage of brain injury or may not appear until later. Treatment includes shunting and draining of CSF as well as treatment for the root cause of the condition.

Another complication is when CSF leaks occur following tearing of the meningeal layers that cover the brain. This often occurs following skull fracture. A tear between the dura and the arachnoid membranes can cause CSF to leak out of the subarachnoid space into the subdural space. CSF can also leak from the nose and the ear. In addition, tears that allow CSF to leak out of the brain cavity can also allow air and bacteria into the cavity, possibly causing infections such as meningitis. Infections within the intracranial cavity are a dangerous complication of brain injury. They may occur outside of the dura mater, below the dura, below the arachnoid membrane or within the brain itself (abscess). Most of these complications develop within a few weeks of the initial trauma and result from skull fractures or penetrating injuries. Standard treatment involves antibiotics and sometimes surgery to remove the infected tissue. Meningitis may be especially dangerous, with the potential to spread to the rest of the brain and nervous system.

Any damage to the head or brain generally will cause some degree of damage to the vascular system serving the brain. While the body can repair damage to small blood vessels, damage to larger vessels can result in serious complications. For example, damage to one of the major arteries leading to the brain can cause a stroke, either through bleeding from the artery (hemorrhagic stroke) or through the formation of a clot at the site of injury (thrombus or thrombosis), blocking blood flow to the brain (ischemic stroke). Other types of vascular injuries include vasospasm and the formation of aneurysms. The methods of the invention are also suitable for treating stroke and related complications.

Skull fractures, especially at the base of the skull, can cause cranial nerve injuries that result in compressive cranial neuropathies. All but 3 of the 12 cranial nerves project out from the brainstem to the head and face. The seventh cranial nerve, called the facial nerve, is the most commonly injured cranial nerve in brain injury and damage to it can result in paralysis of facial muscles.

Pain, especially headache, is commonly a significant complication for conscious patients following brain injury. Serious complications for patients who are unconscious, in a coma or in a vegetative state include bed or pressure sores, recurrent bladder infections, pneumonia and other life-threatening infections, and progressive multiple organ failure.

Other complications caused by brain injuries include becoming paraplegia or quadriplegia.

TBI is the signature injury of the Iraq conflict (Okie (2005) NEJM 352(20):2043-2047; Okie (2006) NEJM 355: 2609-2615; Vasterling et al, (2006) JAMA 296:519-529; Taber et al, (2006) J Neuropsychiatry Clin Neurosci 18:141-145; Das et al, (2005) NEJM 353: 633-634). TBI and its association with post-traumatic stress disorder (PTS) are in the news every day with the latest information revealing that 30% of the injured military population returns home from Iraq with TBI.

Treatment options for brain injury patients can involve surgery, draining of fluids and rehabilitation. Approximately half of severely head-injured patients will need surgery to remove or repair hematomas or contusions. When an injury occurs inside the skull-encased brain, there is no place for swollen tissues to expand and no adjoining tissues to absorb excess fluid. This increased pressure is called intracranial pressure (ICP) and requires draining of fluid to decrease the ICP. In some instances drugs such as mannitol or barbiturates can be used to decrease ICP. The cognitive and communication problems associated with brain injury are best treated as soon after the injury as possible. This early therapy will frequently center on increasing skills of alertness and attention, improving orientation to person, place, time, and situation, and stimulating speech understanding. Longer term rehabilitation may be performed depending upon the needs of the individual.

To date, no treatment option exists that is able to ameliorate cellular damage following brain injury, provide neuroprotection or induce the growth and development of new brain cells to replace damaged brain cells, any or all of which could help return the injured patient to normal or near normal function. Therefore, it is an object of the instant invention to provide such treatment options for brain injury patients.

Nervous System Disease

There are many different types of diseases of the nervous system. Some of these affect the central nervous system (i.e. ALS, Huntington's Disease, Parkinson's Disease), while others affect the peripheral nervous system (i.e. peripheral neuropathies). In most cases, regardless of the cause, the result of the disease is generally neurodegeneration and neuron death with associated loss of functional. Many treatments have been investigated, such as neurotrophic factors, most with limited success. In addition, various types of stem cells and cells having stem-like qualities are being investigated for their potential to treat and perhaps cure many diseases and disorders of the nervous system.

Over the past several decades, the concept of neural tissue grafting or exogenous stem cell transplantation has been investigated for its potential to treat central nervous system disorders. Current stem cell approaches have resulted in some limited therapeutic success but the establishment of long-term functional replacement is variable. It generally appears that the transplanted cells do not form or maintain the functional contacts essential for neuronal cell survival.

Much research has focused on driving the differentiation of stem cells in vitro using various growth factors and differentiation factors prior to implanting the cells. Other research has focused on driving the differentiation of stem cells in vivo, after implantation. Unfortunately, these methods have generated very little in the way of therapeutic successes to date.

Research suggests that several growth and differentiation factors may be involved in the proliferation, differentiation, migration and integration of stem cells into neural cells or tissues and that the particular factor, or combination of factors, may vary based on the type of neural cell desired (i.e. neuron, glial cell, etc.).

Examples of factors that encourage proliferation/expansion include IL-3, SCF, Flt-3 ligand, PDGF, EGF and FGF-2. A combination of several may be applied. For example, neuronal precursor cells have been expanded in the presence of both EGF and FGF-2. A specific example is provided by Lazzari, L., et al. (2001, Br J Haematol. 112(2):397-404) wherein, the highest expansion of cord blood hematopoietic stem cells was obtained with a combination containing Flt-3 ligand, thrombopoietin, IL-6 and IL-11.

Transcription factors such as Pax6 and Emx2 may be required for proliferation and patterning during neuronal development. Sonic hedgehog (SHH) is well known for its control of numerous processes during development as well as acting as a mitogen for embryonic neural stem cells. SHH may induce proliferation of adult stem cells. In the adult CNS, the actions of BMP and noggin are believed to regulate the balance between neurons and astrocytes.

TGF-β family members have been shown to have differentiation effects on ES cells (Schuldiner M., et al, PNAS USA. 2000 97(21):11307-12.) and neural crest stem cell differentiation (Shah N. M. Cell. 1996, 85(3):331-43; White P. M. Neuron. 2001, 29(1):57-71). Other agents that contribute to differentiation are Wnt factors, integrins, and extracellular matrix components. A mix of factors may be applied to differentiate a group of stem cells into a particular type of neuron. For example, FGF-2, ascorbic acid, SHH and FGF-8 have been used to differentiate mouse ES cells into dopaminergic and serotonergic neurons (Lee S. M. Nat Biotechnol. 2000, 18(6):675-9).

Unfortunately, to date, no treatment option exists that is able to ameliorate cellular damage associated with CNS disorders, provide neuroprotection to minimize additional cell damage or death, or induce the growth and development of new CNS cells to replace damaged, diseased or non-functional CNS cells, any or all of which could help return the patient to normal or near normal function. Therefore, it is an object of the instant invention to provide such treatment options for patients suffering CNS disorders.

BRIEF SUMMARY OF THE INVENTION

It is an object of the instant invention to provide novel methods for treating nervous system injury, including traumatic injuries to nervous tissue, in particular traumatic brain injury, and degenerative diseases and disorders of the central and peripheral nervous system. Such methods utilize novel compositions including trophic factor secreting extraembryonic cells (herein referred to as TSE cells), conditioned media and cell products derived therefrom, each alone and/or in combination with each other and/or with other agents including active and/or inactive agents. In a particular embodiment, the methods utilize novel compositions including, but not limited to, amnion-derived multipotent progenitor cells (herein referred to as AMP cells), conditioned media derived therefrom (herein referred to as amnion-derived cellular cytokine solution or ACCS), and cell products derived therefrom, each alone and/or in combination with each other and/or with other agents including active and/or inactive agents. In a certain embodiment, the AMP cells are pooled AMP cells and the ACCS is pooled ACCS.

Applicants demonstrate herein for the first time that AMP cells and/or ACCS are able to effect neuroprotection and/or recovery in an animal model of traumatic brain injury as evidenced by 1) AMP cell migration induced by traumatic brain injury as well as neuroprotective effects which are not limited to the area where migrated AMP cells are present, suggesting that the attenuation of the secondary brain injury may be mediated by mechanisms such as the sustained secretion of neurotrophic factors AMP cells have been demonstrated herein to secrete in physiological levels; 2) the use of a solidified collagen-based scaffold in an animal model of PBBI which provides a supportive matrix for AMP cell survival, migration, and neuroprotection when injected along the PBBI tract immediately after injury; and 3) in spinal cord injury models, wherein improvement in behavioral testing following treatment with AMP cells is evidenced by a gain of coordinated locomotion.

Accordingly, a first aspect of the invention is a method for stimulating growth or regeneration of neuronal cells in a patient in need thereof comprising administering to the patient a therapeutically effective amount of one or more compositions comprising TSE cells, conditioned media derived therefrom, cell lysate derived therefrom or cell products derived therefrom.

A second aspect of the invention is a method for preventing or ameliorating neurodegeneration of neuronal cells in a patient in need thereof comprising administering to the patient a therapeutically effective amount of one or more compositions comprising TSE cells, conditioned media derived therefrom, cell lysate derived therefrom or cell products derived therefrom. In a specific embodiment the neurodegeneration of neuronal cells is axonal degeneration.

A third aspect of the invention is a method for treating brain injury in a patient in need thereof comprising administering to the patient a therapeutically effective amount of one or more compositions comprising TSE cells, conditioned media derived therefrom, cell lysate derived therefrom or cell products derived therefrom. In specific embodiments the brain injury is a traumatic brain injury or injury caused by a disease or disorder.

Specific embodiments of traumatic brain injury include skull fracture or penetration injury. In particular embodiments the traumatic brain injury is a closed injury such as Shaken Baby Syndrome, blast injury, blunt trauma, concussion, concussion syndrome or stroke.

In specific embodiments of nervous system diseases or disorders, the disease or disorder is due to neurotoxins, infections, tumors, metabolic abnormalities, or genetic abnormalities. In other specific embodiments the disease or disorder is a degenerative disease, a motor neuron disease, a demyelinating disease, or a peripheral neuropathy.

In particular embodiments of disease or disorder, the degenerative disease is Alzheimer's disease, Frontotemporal dementia, Parkinson's disease or Huntington's disease; the motor neuron disease is Amyotrophic Lateral Sclerosis, Spinal Muscular Atrophy, Progressive Bulbar Palsy, Primary Lateral Sclerosis, Progressive Pseudobulbar Palsy or Post-polio Syndrome; the demyelinating disease is Multiple Sclerosis, Balo's Concentric Sclerosis, Acute Disseminating Encephalomyelitis, Neuromyelitis Optica, Transverse Myelitis or Leukodystrophies; and the peripheral neuropathy is inherited (HNPP, CMT1A, CMT1B, DSS, CMT1X, CMT4B1), infectious (Leprosy, HIV), immune (GBS), diabetic (Type I, Type II), injury (transient nerve crush, chronic constriction injury, partial nerve ligation, spinal nerve ligation, spared nerve injury), and chemotherapy (i.e. cisplatin)-induced neuropathies.

In specific embodiments of aspects one, two and three of the invention the TSE cells are AMP cells. In a particular embodiment the AMP cells are pooled AMP cells. In still other embodiments the AMP cells are undifferentiated, partially differentiated or fully differentiated, or combinations thereof. In another specific embodiment of aspects one, two and three the conditioned media is ACCS. In a particular embodiment the ACCS is pooled ACCS. In yet another embodiment the TSE cells, conditioned media derived therefrom, cell lysate derived therefrom or cell products derived therefrom are administered in combination with other agents, including active agents such as neuroprotective agents, growth factors, cytokines, chemokines, antibodies, antibiotics, anti-fungals, anti-virals or other cell types, and non-active agents such as matrix, in particular, collagen matrix.

Other features and advantages of the invention will be apparent from the accompanying description, examples and the claims. The contents of all references, pending patent applications and published patents, cited throughout this application are hereby expressly incorporated by reference. In case of conflict, the present specification, including definitions, will control.

Definitions

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "trophic factor-secreting extraembryonic cells" or "TSE cells" means a population of cells derived from the extraembryonic tissue which have the characteristic of secreting at least one factor from the group bNGF, βNGF, FGF-4, IGF-II, HGF, BDNF, GDNF, FGF-2 (bFGF), IGF-II, CNTF, LIF, GITRL, GITR, M-CSF, GRO, GROα, HGF, Thymosin β4, ICAM-2, EGF-R and EGF, and at least one factor from the group Angiogenin, TGFβ2, PDGF, VEGF, TIMP-1 and TIMP-2, wherein each secreted factor is secreted at physiologically relevant levels in a physiologically relevant temporal manner into the extracellular space or into the surrounding culture media. In another embodiment, the TSE cells secrete more than one factor from the group bNGF, βNGF, FGF-4, IGF-II, HGF, BDNF, GDNF, FGF-2 (bFGF), IGF-II, CNTF, LIF, GITRL, GITR, M-CSF, GRO, GROα, HGF, Thymosin β4, ICAM-2, EGF-R and EGF, and at least one factor from the group Angiogenin, TGFβ2, PDGF, VEGF, TIMP-1 and TIMP-2, wherein each secreted factor is secreted physiologically relevant temporal manner into the extracellular space or into surrounding culture media. In another embodiment, the TSE cells secrete bNGF, βNGF, FGF-4, IGF-II, HGF, BDNF, GDNF, FGF-2 (bFGF), IGF-II, CNTF, LIF, GITRL, GITR, M-CSF, GRO, GROα, HGF, Thymosin β4, ICAM-2, EGF-R and EGF, and at least one factor from the group Angiogenin, TGFβ2, PDGF, VEGF, TIMP-1 and TIMP-2, wherein each secreted factor is secreted physiologically relevant levels in a physiologically relevant temporal manner into the extracellular space or into surrounding culture media. TSE cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of clinically relevant TSE cells that are epithelial cells derived from the amnion. In addition to the characteristics described above for TSE cells, AMP cells have the following characteristics. They have not been cultured in the presence of any animal-derived products, making them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666,949, 60/699,257, 60/742,067, U.S. Provisional Application Nos. 60/813,759, U.S. application Ser. No. 11/333,849, U.S. application Ser. No. 11/392,892, and PCTUS06/011392, each of which is incorporated herein in its entirety).

By the term "animal-free" when referring to compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized. As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from TSE cells, including AMP cells.

As used herein, the term "amnion-derived cellular cytokine solution" or "ACCS" means conditioned medium that has been derived from AMP cells or expanded AMP cells. Amnion-derived cellular cytokine solution has previously been referred to as "amnion-derived cellular cytokine suspension".

The term "physiological level" as used herein means the level that a substance in a living system is found and that is relevant to the proper functioning of a biochemical and/or biological process.

As used herein, the term "pooled" means a plurality of compositions that have been combined to create a new composition having more constant or consistent characteristics as compared to the non-pooled compositions. For example, pooled AMP cells have more constant or consistent characteristics compared to non-pooled AMP cells.

The term "therapeutically effective amount" means that amount of a therapeutic agent necessary to achieve a desired physiological effect (i.e. promote neuroprotection).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

"Neural tissue" or "nervous tissue" includes any tissue that comprises a neural cell or a nerve. Other cells that may be present include one or more of oligodendrocytes, astrocytes, ependymal cells, microglial cells or Schwann cells.

As used herein the term "nervous system" means all cells and tissues that comprise the brain, spinal cord and peripheral nerves. The term "central nervous system" or "CNS" means the brain and/or spinal cord, and the term "peripheral nervous system" or "PNS" means all cells and tissues which comprise the peripheral nerves.

As used herein, "nervous system disorder" means any condition or disease that causes or results in a functional and/or physical deficit in the central and/or peripheral nervous system. As used herein, "central nervous system disorder" or "CNS disorder" means any condition or disease that causes or results in a functional and/or physical deficit in the brain and/or spinal cord and "peripheral nervous system disorder" or "PNS disorder" means any condition or disease that causes or results in a functional and/or physical deficit in the cells and tissues which comprise the peripheral nerves.

The term "brain injury" refers to any and all injury of the brain and can be caused by fracture or penetration of the skull (i.e. a vehicle accident, fall, gunshot wound), a disease process (i.e. neurotoxins, infections, tumors, metabolic abnormalities, etc.) or a closed head injury such as in the case of rapid acceleration or deceleration of the head (i.e. Shaken Baby Syndrome, blast), blunt trauma, concussions, and concussion syndrome.

As used herein, the term "neuroprotection" means the arrest and/or reverse progression of neurodegeneration. As used herein, the term "neurodegeneration" means the progressive loss of neurons. This includes but is not limited to immediate loss of neurons followed by subsequent loss of connecting or adjacent neurons.

"Neuron," "neuronal cell" and "neural cell" (including neural progenitor cells and neural stem cells) are used interchangeably to refer to nerve cells, i.e., cells that are responsible for conducting nerve impulses from one part of the body to another. Most neurons consist of three distinct portions: a cell body which contains the nucleus, and two different types of cytoplasmic processes: dendrites and axons. Dendrites, which are the receiving portion of the neuron, are usually highly branched, thick extensions of the cell body. The axon is typically a single long, thin process that is specialized to conducts nerve impulses away from the cell body to another neuron or muscular or glandular tissue. Axons may have side branches called "axon collaterals." Axon collaterals and axons may terminate by branching into many fine filaments called telodendria. The distal ends of telodendria are called synaptic end bulbs or axonal terminals, which contain synaptic vesicles that store neurotransmitters. Axons may be surrounded by a multilayered, white, phospholipid, segmented covering called the myelin sheath, which is formed by Schwann cells in the peripheral nervous system and oligodendrocytes in the central nervous system. Axons containing such a covering are "myelinated." Neurons include sensory (afferent) neurons, which transmit impulses from receptors in the periphery to the brain and spinal cord and from lower to higher centers of the central nervous system. A neuron can also be motor (efferent) neurons which convey impulses from the brain and spinal cord to effectors in the periphery and from higher to lower centers of the central nervous system. Other neurons are association (connecting or interneuron) neurons which carry impulses from sensory neurons to motor neurons and are located within the central nervous system. The processes of afferent and efferent neurons arranged into bundles are called "nerves" when located outside the CNS or fiber tracts if inside the CNS.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein, the term "scar" or "scarring" refers to a residual left by the healing of injured tissue. The residual can be manifested by a visible mark, by color, by palpable thickness, or by lack of compliance, or plasticity, or functional deficit. As used herein, the term "improved scar" or "improved scarring" or "reduced scarring" means that an injured tissue which has been treated with an agent capable of altering scar formation develops a residual that is less visible, or less thick, or more pliable and elastic, or possesses meaningful function, and is more like normal tissue than injured tissue that has not been treated by the agent.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, the preferred methods and materials are now described.

It must be noted that as used herein and in the appended claims, the singular forms "a," "and" and "the" include plural references unless the context clearly dictates otherwise.

Therapeutic Uses

Brain injury is any injury to the brain and can be caused by fracture or penetration of the skull, a disease process, or a closed head injury such as rapid acceleration or deceleration of the head.

Traumatic Brain Injuries (TBI)—can result from a closed head injury or a penetrating head injury. A closed injury occurs when the head suddenly and violently hits an object but the object does not break through the skull. A penetrating injury occurs when an object pierces the skull and enters brain tissue. Skull fractures occur when the bone of the skull cracks or breaks. A depressed skull fracture occurs when pieces of the broken skull press into the tissue of the brain. A penetrating skull fracture occurs when something pierces the skull, such as a bullet, leaving a distinct and localized injury to brain tissue. Skull fractures can cause cerebral contusion.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients, or in people who suffer significant blood loss from other injuries that decrease blood flow to the brain.

All of the above result in neurodegeneration which is the progressive loss of neurons in the brain. Multiple physiological events lead to the neurodegeneration of the brain tissues following a traumatic injury. These events include, for example, cerebral edema, destruction of vascular integrity, increases in the immune and inflammatory response, demyelinization, and lipid peroxidation. Hence, the methods of the instant invention are useful in reducing and/or preventing the physiological events leading to such neurodegeneration. Specifically, the present invention provides methods for reducing or eliminating neuronal cell death (directly or indirectly), edema, ischemia, and enhancing tissue viability following a traumatic injury to the central nervous system.

Degenerative Diseases of the Nervous System

Alzheimer's Disease—Alzheimer's disease (AD), the most common type of dementia, is a neurodegenerative disease characterized by progressive cognitive deterioration together with declining activities of daily living and neuropsychiatric symptoms or behavioral changes. The most obvious early symptom is loss of short-term memory, which usually manifests as minor forgetfulness that becomes steadily more pronounced, with relative preservation of older memories. As the disease progresses, cognitive impairment extends to language, skilled movements, recognition, and functions such as decision-making and planning. The pathological process consists primarily of neuronal loss or atrophy, mainly in the temporoparietal cortex, but also in the frontal cortex, together with an inflammatory response to the deposition of amyloid plaques and neurofibrillary tangles.

While the ultimate cause of AD is unknown, genetic factors are known to be important and dominant mutations in three different genes have been identified that account for a much smaller number of cases of familial, early-onset AD. For the more common form of late onset AD, ApoE is the only repeatibly confirmed susceptibility genes for AD.

At autopsy, both amyloid plaques and neurofibrillary tangles are clearly visible by microscopy. At an anatomical level, AD is characterized by gross diffuse atrophy of the brain and loss of neurons, neuronal processes and synapses in the cerebral cortex and certain subcortical regions. This results in gross atrophy of the affected regions.

Current treatment involves acetylcholinesterase inhibitors (i.e. donepezil (Aricept), galantamine (Razadyne) and rivastigmine (Exelon)), the natural extract Gingko Biloba, NMDA antagonists (i.e. memantine (Akatinol, Axura, Ebixa, and Namenda)), and psychosocial intervention (i.e. counseling, psychotherapy, reminiscent therapy, reality orientation, behavioral reinforcements and cognitive rehabilitation training). The compositions and methods of the present invention are effective in treating AD.

Frontotemporal dementia (FTD)—describes a clinical syndrome associated with shrinking of the frontal and temporal anterior lobes of the brain (formerly known as Pick's disease). The current designation of the syndrome groups together Pick's disease, primary progressive aphasia, and semantic dementia as FTD. Some doctors propose adding corticobasal degeneration and progressive supranuclear palsy to FTD and calling the group Pick Complex. As it is defined today, the symptoms of FTD fall into two clinical patterns that involve either (1) changes in behavior, or (2) problems with language. The first type features behavior that can be either impulsive (disinhibited) or bored and listless (apathetic). The second type primarily features symptoms of language disturbance, including difficulty making or understanding speech, often in conjunction with the behavioral type's symptoms. Spatial skills and memory remain intact. There is a strong genetic component to the disease and FTD often runs in families. The compositions and methods of the present invention are effective in treating FTD.

Parkinson's Disease—is caused by the progressive impairment or deterioration of neurons in an area of the brain known as the substantia nigra. When functioning normally, these neurons produce a vital brain chemical known as dopamine. Dopamine serves as a chemical messenger allowing communication between the substantia nigra and another area of the brain called the corpus striatum. This communication coordinates smooth and balanced muscle movement. A lack of dopamine results in abnormal nerve functioning, causing a loss in the ability to control body movements.

Parkinson's disease is currently treated with drugs or, in some cases, surgery. Two general approaches to the treatment of Parkinson's disease with medication are 1) slow the loss of dopamine in the brain and 2) improve the symptoms of Parkinson's disease. Most patients with Parkinson's disease can be adequately treated with medications that alleviate their symptoms. If medications are not sufficiently effective, new, highly effective and safe surgical treatments are also available. Drugs currently available to treat Parkinson's disease include Sinemet (levodopa/carbidopa) Levodopa (also called L-dopa), which is the most commonly prescribed and most effective medication for controlling the symptoms of Parkinson's disease; Symmetrel, which may be helpful for people with mild Parkinson's disease, but it often causes significant side-effects including confusion and memory problems; Anticholinergics (Artane, Cogentin) are used to restore the balance between the two brain chemicals, dopamine and acetylcholine, by reducing the amount of acetylcholine. These medications, however, can impair memory and thinking, especially in older people; therefore, they are rarely used today; Eldepryl and Deprenyl are two names for the same drug. They work by helping to conserve the amount of dopamine available by preventing the dopamine from being destroyed. While controversial, there is some evidence that this drug may slow the progression of Parkinson's disease, particularly early in the course of the disease. This drug is well-tolerated by most people, so many experts recommend using it despite the controversies. Tasmar, Comtan (COMT Inhibitors). When COMT is blocked, dopamine can be retained and used more effectively, reducing Parkinson's symptoms. COMT inhibitors can also increase the effectiveness of levodopa.

Surgical options include deep brain stimulation which is a method to inactivate the parts of the brain that cause Parkinson's disease and its associated symptoms without purposefully destroying the brain. In deep brain stimulation, electrodes are placed in the globus pallidus. The electrodes are connected by wires to a type of pacemaker device (called an impulse generator, or IPG) that is implanted under the skin of the chest. Once activated, the device sends continuous electrical pulses to the target areas in the brain, blocking the impulses that cause tremors. This has the same effect as thalamotomy or pallidotomy surgeries without actually destroying parts of the brain. The stimulation can be turned on or off by the patient with a hand-held magnet or an access control device. The compositions and methods of the present invention are effective in treating Parkinson's disease.

Huntington's disease (HD)—results from genetically programmed degeneration of neurons in certain areas of the brain. This degeneration causes uncontrolled movements, loss of intellectual faculties, and emotional disturbance. HD is a familial disease, passed from parent to child through a mutation in the normal gene. Each child of an HD parent has a 50-50 chance of inheriting the HD gene. If a child does not inherit the HD gene, he or she will not develop the disease and cannot pass it to subsequent generations. A person who inherits the HD gene will sooner or later develop the disease. Some early symptoms of HD are mood swings, depression, irritability, learning new things, remembering a fact, or making a decision. As the disease progresses, concentration on intellectual tasks becomes increasingly difficult and the patient may have difficulty feeding himself and swallowing. The rate of disease progression and the age of onset vary from person to person.

Current treatments for HD address the symptoms, not the underlying disease itself. For example, tranquilizers such as clonazepam (Klonopin) and antipsychotic drugs such as haloperidol (Haldol) and clozapine (Clozaril) are used to help control movements, violent outbursts and hallucinations. Other drugs such as fluoxetine (Prozac, Sarafem), sertraline (Zoloft) and nortriptyline (Aventyl, Pamelor), are used to help control depression and the obsessive-compulsive behaviors often exhibited by some HDS patients. Medications such as lithium (Eskalith, Lithobid) can help control extreme emotions and mood swings. Side effects from the drugs used to treat the symptoms of HD include hyperexcitability, fatigue and restlessness. In some instances, antipsychotic drugs may cause side effects that mimic the signs of Parkinson's disease, including involuntary twitching of the face and body (tardive dyskinesia). Because HD can impair speech therapy is often prescribed. The compositions and methods of the present invention are effective in treating HD.

Motor Neuron Diseases

Amyotrophic lateral sclerosis (ALS)—sometimes called Lou Gehrig's disease, is a progressive, fatal neurodegenerative disease caused by the degeneration of motor neurons. ALS is marked by gradual degeneration of the neurons in the CNS that control voluntary muscle movement. The disorder causes muscle weakness and atrophy throughout the body. In ALS, both the upper motor neurons and the lower motor neurons degenerate or die, ceasing to send messages to muscles. Unable to function, the muscles gradually weaken and atrophy. Eventually, the brain completely loses its ability to initiate and control voluntary movement. The disease does not necessarily debilitate the patient's mental functioning in the same manner as Alzheimer's disease or other neurological conditions do. Instead, those suffering advanced stages of the disease may retain the same memories, personality, and intelligence they had before its onset.

Current treatment for ALS is very limited. One drug, riluzole (Rilutek®) is believed to reduce damage to motor neurons and prolong survival by several months, mainly in those with difficulty swallowing. Another drug, gabapentin (Neurotin®), is a seizure medication and is believed to work to reduce glutamate production. It may be beneficial to some ALS patients. The compositions and methods of the present invention are effective in treating ALS.

Spinal muscular atrophy (SMA)—is a genetic, motor neuron disease caused by progressive degeneration of motor neurons in the spinal cord. The disorder causes weakness and wasting of the voluntary muscles. Weakness is often more severe in the legs than in the arms. The childhood SMAs are all autosomal recessive diseases. This means that they run in families and more than one case is likely to occur in siblings or cousins of the same generation. There are many types of SMA; some of the more common types are as follows: SMA type I, also called Werdnig-Hoffmann disease, is evident before birth or within the first few months of life. There may be a reduction in fetal movement in the final months of pregnancy. Symptoms include floppiness of the limbs and trunk, feeble movements of the arms and legs, swallowing and feeding difficulties, and impaired breathing.

Affected children never sit or stand and usually die before the age of 2. Symptoms of SMA type II usually begin between 3 and 15 months of age. Children may have respiratory problems, floppy limbs, decreased or absent deep tendon reflexes, and twitching of arm, leg, or tongue muscles. These children may learn to sit but will never be able to stand or walk. Life expectancy varies. Symptoms of SMA type III (Kugelberg-Welander disease) appear between 2 and 17 years of age, and include abnormal manner of walking; difficulty running, climbing steps, or rising from a chair; and slight tremor of the fingers. Kennedy syndrome or progressive spinobulbar muscular atrophy may occur between 15 and 60 years of age. Features of this type may include weakness of muscles in the tongue and face, difficulty swallowing, speech impairment, and excessive development of the mammary glands in males. The course of the disorder is usually slowly progressive. Congenital SMA with arthrogryposis (persistent contracture of joints with fixed abnormal posture of the limb) is a rare disorder. Manifestations include severe contractures, curvature of the spine, chest deformity, respiratory problems, an unusually small jaw, and drooping upper eyelids.

There are no drugs for treating SMA, although much can be done to manage patients medically, in particular, managing respiratory, nutritional and rehabilitation care. There are several drugs currently under investigation, including butyrates, valproic acid, hydroxyurea and riluzole. The compositions and methods of the present invention are effective in treating SMAs.

Progressive bulbar palsy—is a disorder in which the nerves controlling the muscles of chewing, swallowing, and talking are affected, making these functions increasingly difficult. Because swallowing is difficult, food or saliva is often inhaled (aspirated) into the lungs, causing choking or gagging and increasing the risk of pneumonia. Death, which is often due to pneumonia, usually occurs 1 to 3 years after the disorder begins. Most treatment is directed to managing symptoms. Riluzole may be effective in certain patients. The compositions and methods of the present invention are effective in treating progressive bulbar palsy.

Primary Lateral Sclerosis and Progressive Pseudobulbar Palsy—are rare, slowly progressive variants of amyotrophic lateral sclerosis. Primary lateral sclerosis affects mainly the arms and legs, and progressive pseudobulbar palsy affects mainly the muscles of the face, jaw, and throat. Emotions may be changeable. Inappropriate emotional outbursts are common. In both disorders, severe stiffness accompanies muscle weakness. The disorders usually progress for several years before total disability results. Most treatment is directed to managing symptoms. Riluzole may be effective in certain patients. The compositions and methods of the present invention are effective in treating primary lateral sclerosis and progressive pseudobulbar palsy.

Post-polio syndrome—Some people who have had polio may develop tired, painful, and weak muscles 15 years or more after their recovery from polio. Sometimes muscle tissue also wastes away, suggesting a reactivation of the polio infection. There are no specific treatments for post-polio syndrome. Most treatments are directed to treating symptoms. The three primary symptoms that are treated with medication are weakness of muscle, fatigue (individual muscle and generalized), and pain, i.e., post-polio pain, overuse pain, bio-mechanical pain, and bone pain. The compositions and methods of the present invention are effective in treating post-polio syndrome.

Demyelinating Diseases

A. Acquired

Multiple Sclerosis (MS)—is an unpredictable disease of the central nervous system that can range from relatively benign to somewhat disabling to devastating, as communication between the brain and other parts of the body is disrupted. Many investigators believe MS to be an autoimmune disease in which the nerve-insulating myelin is attacked. Most people experience their first symptoms of MS between the ages of 20 and 40 and the initial symptom of MS is often blurred or double vision, red-green color distortion, or even blindness in one eye. Most patients experience muscle weakness in their extremities and difficulty with coordination and balance. The symptoms may be severe enough to impair walking or even standing and in the worst cases, can produce partial or complete paralysis. Most people with MS also exhibit paresthesias. Speech impediments, tremors, and dizziness are other frequent complaints and occasionally, patients experience hearing loss. Approximately half of all people with MS experience cognitive impairments such as difficulties with concentration, attention, memory, and poor judgment, but such symptoms are usually mild. Several forms of MS exist including Benign MS, Relapsing Remitting MS (the most common form), Secondary Progressive MS, Primary Progressive MS, Malignant MS (Marburg variant) and Chronic MS.

Several drugs are available to treat MS, including interferon beta-1b (Betaseron®), interferon beta-1a (Avonex®), high dose/frequency interferon beta-1a (Rebif®), glatiramer (Copaxone®), mitoxantrone (Novantrone®) and corticosteroids. The compositions and methods of the present invention are effective in treating MS.

Balo's concentric sclerosis (Balo Disease)—is a rare and progressive variant of MS. It usually first appears in adulthood, but childhood cases have also been reported. While MS typically is a disease that waxes and wanes, Balo concentric sclerosis is different in that it tends to be rapidly progressive. Symptoms may include headache, seizures, gradual paralysis, involuntary muscle spasms, and cognitive loss. The disease is characterized by bands of intact myelin (the sheath of fatty substances surrounding nerve fibers) alternating with rings of loss of myelin (demyelination) in various parts of the brain and brain stem. Symptoms may progress rapidly over several weeks or more slowly over two to three years. The same drugs used to treat MS are used to treat Balo Disease. The compositions and methods of the present invention are effective in treating Balo's concentric sclerosis.

Acute disseminating encephalomyelitis (ADEM)—is characterized by a brief but intense attack of inflammation in the brain and spinal cord that damages myelin. It often follows viral infection, or less often, vaccination for measles, mumps, or rubella. The symptoms of ADEM come on quickly, beginning with encephalitis-like symptoms such as fever, fatigue, headache, nausea and vomiting, and in severe cases, seizures and coma. It may also damage white matter, leading to neurological symptoms such as visual loss in one or both eyes, weakness even to the point of paralysis, and difficulty coordinating voluntary muscle movements. ADEM is sometimes misdiagnosed as a severe first attack of MS. However, ADEM usually has symptoms of encephalitis (such as fever or coma), as well as symptoms of myelin damage (visual loss, paralysis). In addition, ADEM usually consists of a single episode or attack, while MS features many attacks over the course of time. Children are more likely than adults to have ADEM. The compositions and methods of the present invention are effective in treating ADEM.

Neuromyelitis Optica (Devic's Disease)—is an inflammatory disease of the CNS in which there are episodes of inflammation and damage to the myelin that almost exclusively affect the optic nerves and spinal cord. It usually causes temporary blindness, occasionally permanent, in one or both eyes. It can also lead to varying degrees of weakness or paralysis in the legs or arms, loss of sensation, and/or bladder and bowel dysfunction from spinal cord damage. The compositions and methods of the present invention are effective in treating neuromyelitis optica.

Transverse myelitis (TM)—is a neurologic syndrome caused by inflammation of the spinal cord. TM is uncommon but not rare. The term myelitis is a nonspecific term for inflammation of the spinal cord; transverse refers to involvement across one level of the spinal cord. It occurs in both adults and children. The compositions and methods of the present invention are effective in treating transverse myelitis.

B. Hereditary

Leukodystrophies—refers to a group of disorders characterized by progressive degeneration of the white matter of the brain. The leukodystrophies are caused by imperfect growth or development of the myelin sheath. Myelin is a complex substance made up of at least ten different molecules. Each of the leukodystrophies is the result of a defect in the gene that controls the production or metabolism of one (and only one) of the component molecules of myelin. The different types of leukodystrophy including adrenoleukodystrophy, metachromatic leukodystrophy, Krabbe disease, Pelizaeus-Merzbacher disease, Canavan disease, childhood ataxia with central hypomyelination (CACH or vanishing white matter disease), Alexander disease, Refsum disease and cerebrotendineous xanthomatosis. The compositions and methods of the present invention are effective in treating leukodystrophies.

Peripheral Diseases

Peripheral neuropathy, in its most common form, causes pain and numbness in the hands and feet. The pain typically is described as tingling or burning, while the loss of sensation often is compared to the feeling of wearing a thin stocking or glove. Peripheral neuropathy can result from such problems as traumatic injuries (i.e. axotomy distal to the dorsal root ganglia) or surgical incisions, compression of nerves (i.e. Tic douloureux), post-herpetic infections (i.e. herpes zoster infection), HIV infection, metabolic problems (i.e. diabetes), hereditary sensory and autonomic neuropathies, exposure to toxins (i.e. neurotoxic chemotherapy induced peripheral neuropathy), and drugs (i.e. antiretroviral drugs). In many cases, peripheral neuropathy symptoms improve with time, especially if it is caused by an underlying condition that can be resolved or at least managed. Medications initially designed to treat other conditions, such as epilepsy and depression, are often used to reduce the painful symptoms of peripheral neuropathy. However, treatment options are still limited. The compositions and methods of the present invention are effective in treating peripheral neuropathy.

Obtaining and Culturing of Cells

Identifying TSE cells—Once extraembryonic tissue is isolated, it is necessary to identify which cells in the tissue have the characteristics associated with TSE cells (see definition above). For example, cells are assayed for their ability to secrete one or more of the factors I bNGF, βNGF, FGF-4, IGF-II, HGF, BDNF, GDNF, FGF-2 (bFGF), IGF-II, CNTF, LIF, GITRL, GITR, M-CSF, GRO, GROα, HGF, Thymosin β4, ICAM-2, EGF-R and EGF, and at least one factor from the group Angiogenin, TGFβ2, PDGF, VEGF, TIMP-1 and TIMP-2 into the extracellular space or into surrounding culture media. In some instances, it may be difficult or impossible to detect certain factors using standard assays. This may be because certain factors are secreted by the cells at physiological levels that are below the level of detection by the assay methods. It may also be that the factor(s) is being utilized by the TSE cell and/or by other local cells, thus preventing accumulation at detectable levels using standard assays. It is also possible that the temporal manner in which the factors are secreted may not coincide with the timing of sampling.

AMP cells—In a particular embodiment, AMP cell compositions are prepared using the steps of a) recovery of the amnion from the placenta, b) dissociation of the cells from the amniotic membrane, c) culturing of the cells in a basal medium with the addition of a naturally derived or recombinantly produced human protein; and optionally d) further proliferation of the cells using additional additives and/or growth factors. Details are contained in US Publication No. 2006-0222634-A1, which is incorporated herein by reference.

AMP cells are cultured as follows: The AMP cells are cultured in a basal medium. Such medium includes, but is not limited to, Epilife (Cascade Biologicals), Opti-pro, VP-SFM, IMDM, Advanced DMEM, K/O DMEM, 293 SFM II (all made by Gibco; Invitrogen), HPGM, Pro 293S-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. Details on this procedure are contained in US Publication No. 2006-0222634-A1, which is incorporated herein by reference.

In a most preferred embodiment, the cells are cultured using a system that is free of animal products to avoid xeno-contamination. In this embodiment, the culture medium is Stemline I or II, Opti-pro, or DMEM, with human albumin added up to concentrations of 10%. Alternatively, UltraCulture may be used, with substitution of transferrin with human recombinant transferrin, and replacement of the bovine albumin (BSA) with human albumin at concentrations of up to 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free. Details on this procedure are contained in US Publication No. 2006-0222634-A1, which is incorporated herein by reference.

In alternative embodiments, where the use of non-human serum is not precluded, such as for in vitro uses, the culture medium may be supplemented with serum derived from mammals other than humans, in ranges of up to 40%.

Additional Proliferation

Optionally, other proliferation factors are used. In one embodiment, epidermal growth factor (EGF), at a concentration of between 0-1 µg/ml is used. In a preferred embodiment, the EGF concentration is around 10 ng/ml. Alternative growth factors which may be used include, but are not limited to, TGFα or TGFβ□ (5 ng/ml; range 0.1-100 ng/ml), activin A, cholera toxin (preferably at a level of about 0.1 µg/ml; range 0-10 µg/ml), transferrin (5 µg/ml; range 0.1-100 µg/ml), fibroblast growth factors (bFGF 40 ng/ml (range 0-200 ng/ml), aFGF, FGF-4, FGF-8; (all in range 0-200 ng/ml), bone morphogenic proteins (i.e. BMP-4) or other growth factors known to enhance cell proliferation.

Generation of Conditioned Medium

TSE conditioned medium—is obtained as described below for ACCS, except that TSE cells are used.

Generation of ACCS—The AMP cells of the invention can be used to generate ACCS. In one embodiment, $1 \times 10^6$ AMP cells/mL are seeded into T75 flasks containing between 5-30 ml culture medium, preferably between 10-25 ml culture medium, and most preferably about 10 ml culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, bioreactors or suspension culture apparatuses, or collecting ACCS from sub-confluent and/or actively proliferating cultures, are also contemplated by the methods of the invention. It is also contemplated by the invention that the ACCS be cryopreserved following collection. It is also contemplated by the invention that ACCS be lyophilized following collection. It is also contemplated that ACCS be formulated in a sustained-released formulation. Skilled artisans are familiar with cryopreservation, lyophilization and sustained-release methodologies.

Formulation

The compositions of the invention can be prepared in a variety of ways depending on the intended use of the compositions. For example, a composition useful in practicing the invention may be a liquid comprising an agent of the invention, i.e. TSE cells, including AMP cells and/or ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even both viscous and muco-adhesive.

Pharmaceutical Compositions

The present invention provides pharmaceutical compositions of TSE cells, including AMP cells and/or ACCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Dosage and Administration

Compositions comprising TSE cells, including AMP cells and/or ACCS may be administered to a subject to provide various cellular or tissue functions, for example, to treat brain injury due to trauma, surgery, etc. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in treating brain injury or restoring a therapeutically important metabolic function. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

One of skill in the art may readily determine the appropriate concentration, or dose, of the TSE cells, including AMP cells, and/or ACCS, for a particular purpose. The skilled artisan will recognize that a preferred dose is one which produces a therapeutic effect, such as neuroprotection or healing of injured nervous cells and tissues, in a patient in need thereof. For example, TSE cells, including AMP cells, are prepared at a concentration of between about $1 \times 10^7 - 1 \times 10^8$ cells/mL, preferably at about $2.5 \times 10^7 - 7.5 \times 10^7$ cells/mL, and most preferably at about $5 \times 10^7$ cells/mL. The volume of cell mixture administered will depend upon several variables and can only be determined by the attending physician at time of use. Such proper doses of the TSE cells, including AMP cells, will require empirical determination based on such variables as the severity and type of disease, injury, disorder or condition being treated; patient age, weight, sex, health; other medications and treatments being administered to the patient; and the like. Conditioned media derived from TSE cells, including ACCS derived from AMP cells, is typically administered at full strength because the cytokines and factors contained therein are present at physiologic levels suitable for healing of injured and diseased cells and tissues (see Steed, D. L., et al, Eplasty 2008, Vol. 8, e19, published online Apr. 7, 2008 for a discussion of such physiologic levels of cytokines and factors in ACCS). Again, the volume of conditioned media, including ACCS, will depend upon the extent of injury or disease being treated, etc., and can only be determined by the attending physician at time of use. One of skill in the art will also recognize that number of doses (dosing regimen) to be administered needs also to be empirically determined based on severity and type of disease, injury, disorder or condition being treated. In a preferred embodiment, one dose is sufficient. Other preferred embodiments contemplate, 2, 3, 4, or more doses.

The present invention provides a method of treating a brain injury by administering to a subject TSE cells, including AMP cells and/or ACCS in a therapeutically effective amount. By "therapeutically effective amount" is meant the dose of TSE cells, including AMP cells and/or ACCS that is sufficient to elicit a therapeutic effect. Thus, the concentration of TSE cells, including AMP cells and/or ACCS in an administered dose unit in accordance with the present invention is effective in the treatment or prevention of neuronal damage that follows an injury to the brain and hence elicits a neuroprotective effect.

In further embodiments of the present invention, at least one additional agent may be combined with the TSE cells, including AMP cells and/or ACCS to enhance healing and functional recovery following brain injury. Such agents include but are not limited to neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types. In particular, the neuroprotective agents is for example a dopamine D3 receptor agonist, the neurotrophic factors are BDNF, NT-3, NT-4, CNTF, NGF, or GDNF; the antibodies are for example IN-1 anti-NOGO antibodies; the inhibitor is for example the PDE4 inhibitor rollipram; the immunosuppressive agents are for example corticosteroids (i.e. glucocorticoids), cyclosporine, tacrolimus, sirolimus, methotrexate, azathiopine, mercatopurine, cytotoxic antibiotics, polyclonal and monoclonal antibodies such as anti-T-cell receptor (CD23) and anti-IL2 receptor (CD25) antibodies, interferon, opioids, TNF binding proteins, mycophenolate, and small biological agents such as FTY720; the antibiotics are for example pikromycin, narbomycin, methymycin, neomethymycin; the steroid is for example methylprednisolone; and the other cell types are for example differentiated AMP cells, or a mixture of differentiated and undifferentiated AMP cells, or a mixture of AMP cells (differentiated and/or undifferentiated) and other cells such as neural stem cells or any other progenitor cell or cells that are treated in such a way as to augment the AMP cells or AMP cell activity. Inactive agents include carriers, diluents, stabilizers, gelling agents, delivery vehicles, ECMs (natural and synthetic), scaffolds, and the like. When the TSE cells, including AMP cells and/or ACCS are administered conjointly with other pharmaceutically active agents, even less of the TSE cells, including AMP cells and/or ACCS may be needed to be therapeutically effective. For further information, see, for example, Maas A. I., Expert Opin Investig Drugs 10: 753-767, 2001.

In addition, the administration of TSE cells, including AMP cells and/or ACCS may be in combination with other treatment modalities, for example, therapeutic cooling following TBI (see, for example, McIntyre, L. A., et al., JAMA, 2003:289:2992-2999).

TSE cells, including AMP cells and/or ACCS can be administered by injection into a target site (for example, and injury site or lesion) of a subject, preferably via a delivery device, such as a tube, e.g., catheter. In a preferred embodiment, the tube additionally contains a needle, e.g., a syringe, through which the TSE cells, including AMP cells and/or ACCS can be introduced into the subject at the desired location. Specific, non-limiting examples of administering TSE cells, including AMP cells and/or ACCS to subjects may also include administration by intrathecal injection, epidural injection, intracerebral injection or infusion. Additional non-limiting examples of administering TSE cells, including AMP cells and/or ACCS include subcutaneous injection, intramuscular injection, intravenous injection, intraarterial intramuscular, intracardiac injection, intradermal injection, or intraperitoneal injection. If in some embodiments, an injectable liquid suspension of TSE cells, including AMP cells can be administered by a continuous drip or bolus.

The timing of administration of TSE cells, including AMP cells and/or ACCS will depend upon the type and severity of the brain injury being treated. In a preferred embodiment, the TSE cells, including AMP cells and/or ACCS, are administered as soon as possible after the brain injury. In other preferred embodiments, the TSE cells, including AMP cells and/or ACCS are administered more than one time following the brain injury.

Scaffolds and Matrices

Alternatively, TSE cells, including AMP cells, may be transplanted into the recipient under conditions in which the cells will proliferate and differentiate to form new cells and tissues thereby providing the physiological processes normally provided by that tissue, or in which they may produce factors that cause the migration and/or differentiation of cells in the area of the transplant. Tissues are an aggregation of similarly specialized cells united in the performance of a particular function. Tissue is intended to encompass all types of biological tissue. Of particular relevance to the instant invention are neural tissues, including the functional cells of the nervous system, neurons, and various supporting cells such as glial cells, oligodendrocytes, and the like.

Useful in the transplantation of TSE cells, including AMP cells, are various types of support matrices. Such support matrices into which the TSE cells, including AMP cells, can be incorporated or embedded include matrices which are recipient-compatible and which degrade into products which are not harmful to the recipient. These matrices provide support and protection for TSE cells, including AMP cells, in vivo and are, therefore, a preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices (see, for example, McHale M K, et al., (2005) Tissue Eng 11:1768-1779; Ellis-Behnke R G, et al., (2006) Proc Natl Acad Sci USA 103:5054-5059; Tang S, et al, (2007) Biomed. Mater.: Mater Tissue Engr Regen Med S135-S141; Tang S, et al., (2007) J Biomed Mater Res A 82:323-335.

Suitable synthetic material for a cell transplantation matrix must be biocompatible to preclude migration and immunological complications, and should be able to support extensive cell growth and differentiated cell function. It should also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991).

Other synthetic biodegradable support matrices include synthetic polymers such as polyanhydrides, polyorthoesters, and polylactic acid (see, for example, Balakrishnan B, Jayakrishnan A. (2005), Biomaterials 26:3941-3951; Chueh S K, et al., (2007), Biomed Mater Eng 17:137-146; Jabbari E, et al., (2005), Biomacromolecules 6:2503-2511; Li Q, et al. (2006) Biomaterials 27: 1027-1034). Further examples of synthetic polymers and methods of incorporating or embedding cells into these matrices are also known in the art. See e.g., U.S. Pat. Nos. 4,298,002 and 5,308,701. Other suitable matrices are bioerodable matrices. An example of such a matrix is one made with alginate and alginate lyase (see, for example, Ashton, R. S., et al., Biomaterials, December 2007, Vol 28, Issue 36, pp. 5518-5525).

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that cytokines, growth factors (i.e. neurotrophic factors) or other bioactive compounds can be incorporated directly into the support matrix so that they are slowly released as the support matrix degrades in vivo. As the cell-polymer structure becomes vascularized and the structure degrades, TSE cells, including AMP cells, may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792,525, 5,965,997, 4,879,237 and 4,789,734).

In another example, the TSE cells, including AMP cells, may be transplanted in a gel matrix (such as Gelfoam from Upjohn Company) which polymerizes to form a substrate in which the cells can grow. A variety of encapsulation technologies have been developed (e.g. Lacy et al., Science 254:1782-84 (1991); Sullivan et al., Science 252:718-712 (1991); WO 91/10470; WO 91/10425; U.S. Pat. Nos. 5,837, 234; 5,011,472; 4,892,538). During open surgical procedures involving direct physical access to the damaged brain tissue, all of the described forms of TSE cell, including AMP cell, delivery preparations are available options. These cells can be repeatedly transplanted at intervals until a desired therapeutic effect, i.e. functional recovery from brain injury, is achieved.

The present invention also relates to the use of TSE cells, including AMP cells, in three dimensional cell and tissue culture systems to form structures analogous to tissue counterparts in vivo. The resulting tissue will survive for prolonged periods of time, and perform tissue-specific functions following transplantation into the recipient host. Methods for producing such structures are described in U.S. Pat. Nos. 5,624,840 and 6,428,802, which are incorporated herein in their entireties.

The three-dimensional matrices to be used are structural matrices that provide a scaffold for the cells, to guide the process of tissue formation. Scaffolds can take forms ranging from fibers, gels, fabrics, sponge-like sheets, and complex 3-D structures with pores and channels fabricated using complex Solid Free Form Fabrication (SFFF) approaches. Cells cultured on a three-dimensional matrix will grow in multiple layers to develop organotypic structures occurring in three dimensions such as ducts, plates, and spaces between plates that resemble sinusoidal areas, thereby forming new organ tissue. Thus, in preferred aspects, the present invention provides a scaffold, multi-layer cell and tissue culture system. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

Examples of such scaffolds include a three-dimensional stromal tissue or living stromal matrix which has been inoculated with stromal cells that are grown on a three dimensional support. The extracellular matrix proteins elaborated by the stromal cells are deposited onto the scaffold, thus forming a living stromal tissue. The living stromal tissue can support the growth of TSE cells, including AMP cells, or partially or fully differentiated cells derived therefrom later inoculated to form the three-dimensional cell culture. Examples of other three dimensional scaffolds are described in U.S. Pat. No. 6,372,494.

The design and construction of the scaffolding to form a three-dimensional matrix is of primary importance. The matrix should be a pliable, non-toxic, injectable porous template for vascular ingrowth. The pores should allow tissue ingrowth such as vascular and/or neural ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function.

For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

A sponge-like structure can also be used to create a three-dimensional framework. The structure should be an open cell sponge, one containing voids interconnected with the surface of the structure, to allow adequate surfaces of attachment for sufficient TSE cells, including AMP cells, or partially or fully differentiated cells derived therefrom, to form a viable, functional implant.

The invention also provides for the delivery of TSE cells, including AMP cells, including compositions described herein, in conjunction with any of the above support matrices as well as in conjunction with amnion-derived membranes. Such membranes may be obtained as a by-product of the process described herein for the recovery of amnion epithelial cells from which AMP cells are selected, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, TSE cells, including AMP cells, may be grown on such membranes, added to the membrane in either an undifferentiated, partially differentiated or fully differentiated form, or TSE cell, including AMP cell, conditioned media (i.e. ACCS) or cell lysates derived from the TSE cells, including AMP cells, may be added to such membranes. Alternatively, amniotic tissue in which amnion epithelial cells have not been stripped away may be used to deliver TSE cells, including AMP cells, to a particular site. In all cases, TSE cells, including AMP cells, used in conjunction with amniotic tissue or other matrices can be used in combination with other therapeutically useful cells and/or cells expressing biologically active therapeutics such as those described in below.

Genetic Engineering of TSE Cells, Including AMP Cells

TSE cells, including AMP cells, may be genetically engineered to produce a particular therapeutic protein. Therapeutic protein includes a wide range of biologically active proteins including, but not limited to, growth factors, neurotrophic factors, enzymes, hormones, cytokines, inhibitors of cytokines, blood clotting factors, peptide growth and differentiation factors.

Methods which are well known to those skilled in the art can be used to construct expression vectors containing a nucleic acid encoding the protein of interest linked to appropriate transcriptional/translational control signals. See, for example, the techniques described in Sambrook et al, 2001, "Molecular Cloning: A Laboratory Manual"; Ausubel, ed., 1994, "Current Protocols in Molecular Biology" Volumes I-III; Celis, ed., 1994.

Suitable methods for transferring vector or plasmids into TSE cells, including AMP cells, or cells differentiated therefrom include lipid/DNA complexes. Suitable reagents include lipofectamine, a 3:1 (w/w) liposome formulation of the poly-cationic lipid 2,3-dioleyloxy-N-[2(sperminecarbox-amido)ethyl]-N,N-d-imethyl-1-propanaminium trifluoroacetate (DOSPA) (Chemical Abstracts Registry name: N-[2-(2,5-bis[(3-aminopropyl)amino]-1-oxpentyl)amino) ethyl-]-N,N-dimethyl-2,3-bis(9-octadecenyloxy)-1-propanamin-trifluoroacetate), and the neutral lipid dioleoyl phosphatidylethanolamine (DOPE) in membrane filtered water. Exemplary is the formulation Lipofectamine 2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Transfection of TSE cells can be performed by electroporation, e.g., as described in Roach and McNeish (Methods in Mol. Biol. 185:1 (2002)). Suitable viral vector systems for producing cells with stable genetic alterations may be based on adenoviruses, lentiviruses, retroviruses and other viruses, and may be prepared using commercially available virus components.

Differentiation of TSE Cells, Including AMP Cells

TSE cells, including AMP cells, or cells that are partially differentiated or fully differentiated therefrom may be useful for administration or transplantation into a subject to provide various cellular or tissue functions specific to the differentiated cell type. For example, in certain embodiments, the present invention provides for administration of neural cells derived from TSE cells, including AMP cells, for treatment of brain injury.

Many methods are known for the differentiation of cells into various cell types. For example, the TSE cells, including AMP cells, may be contacted with various growth factors (termed differentiation factors) that influence differentiation of such cells into particular cell types such as neural cells, hepatocytes, pancreatic cells, vascular endothelial cells, muscle cells and cardiomyocytes. For examples, see US2003/0235563 and US2004/0161419, the contents of which are incorporated herein by reference.

The literature is replete with additional differentiation protocols for embryonic as well as non-embryonic stem or other multipotent cells, including stem cells. One skilled in the art will recognize that any of these protocols can be applied to the TSE cell, including AMP cell, compositions described herein to produce partially or fully differentiated cells for such uses. Exemplary protocols are set forth below:

Ectoderm (neural differentiation). Clusters are removed from the large-scale apparatus and transferred to ultra-low adherence 6-well plates. The differentiation protocol described by Carpenter, M. K. et al. (2001) Exp Neurol 172:383-397 for human embryonic stem cells is followed for differentiation as follows. 10 mM all-trans retinoic acid (RA) will added to the culture medium (80% KO-DMEM, 1 mM glutamine, 0.1 mM β-mercaptoethanol, 1% non-essential amino acids, and 20% FBS) containing these clusters in suspension. After 4 days in suspension, clusters are plated onto poly-L-lysine/fibronectin-coated plates in differentiation medium (DMEM/F-12 with B27 (Gibco), 10 ng/ml human epidermal growth factor (hEGF), 10 ng/ml human basic fibroblast growth factor (hbFGF) (Gibco), 1 ng/ml human platelet-derived growth factor-AA (hPDGF-AA) (R & D Systems), and 1 ng/ml human insulin-like growth factor-1 (hIGF-1) (R & D Systems) for 3 days. After 3 days under these conditions, the cells are harvested for RNA or fixed. Fixed cells are immunostained for nestin, polysialylated neural cell adhesion molecule (PS-NCAM), and A2B5. RNA is analyzed by reverse transcriptase-PCR (RT-PCR) for nestin, GFAP and MAP-2.

Differentiated cells derived from TSE cells, including AMP cells, may be detected and/or enriched by the detection of tissue-specific markers by immunological techniques, such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods.

Alternatively, differentiated cells may be detected using selection markers. For example, TSE cells, including AMP cells, can be stably transfected with a marker that is under the control of a tissue-specific regulatory region as an example, such that during differentiation, the marker is selectively expressed in the specific cells, thereby allowing selection of the specific cells relative to the cells that do not express the marker. The marker can be, e.g., a cell surface protein or other detectable marker, or a marker that can make cells resistant to conditions in which they die in the absence of the marker, such as an antibiotic resistance gene (see e.g., in U.S. Pat. No. 6,015,671).

In addition, the TSE cells, including AMP cells, may be used in in vitro priming procedures that result in neural stem cells becoming neurons when grafted into non-neurogenic or neurogenic areas of the CNS. For details and examples, see US2003/0235563 and US2004/0161419, both which are incorporated herein by reference.

Treatment Kits

The invention also provides for an article of manufacture comprising packaging material and a pharmaceutical composition of the invention contained within the packaging material, wherein the pharmaceutical composition comprises compositions of TSE cells, including AMP cells and/or ACCS. The packaging material comprises a label or package insert which indicates that the TSE cells, including AMP cells and/or ACCS can be used for treating brain injury, for example traumatic brain injury, or nervous system diseases and disorders.

Efficacy Measurements for TBI

Skilled artisans will recognize that any and all of the standard methods and modalities for treating brain injury currently in clinical practice and clinical development are suitable for practicing the methods of the invention. Routes of administration, formulation, co-administration with other agents (if appropriate) and the like are discussed in detail elsewhere herein.

The treatment of a brain injury can be monitored by employing a variety of neurological measurements. For example, a therapeutic response can be monitored by determining if, for example, there is an improvement in the subjects a) maximum daily Glasgow Coma Score; b) duration of coma; 3) daily intracranial pressure—therapeutic intensity levels; 4) extent of cerebral edema/mass effect measured on serial CT scans; and, 5) duration of ventilator support. A brief description of each of these measurements is provided below.

The Glasgow Coma Score (index GCS) is a reflection of the depth of impaired consciousness and is best obtained following initial resuscitation (oxygenation, rehydration and support of blood pressure) but prior to use of sedating drugs, neuromuscular blocking agents, or intubation.

The ICP of patients with severe brain injury is often monitored with an intracranial pressure device. Monitoring ICP can provide a measure of cerebral edema. However, inherent variability and analysis complexities due to therapeutic intervention exist. To adjust for these interventions a therapeutic intensity scale was developed. This scale, known as the Therapeutic Intensity Level (TIL), measures treatment aggressiveness for elevated ICPs (Allolio et al. (1995) European Journal of Endocrinology 133(6): 696-700; Adashi et al. (1996) Reproductive endocrinology, surgery, and technology Philadelphia: Lippincott-Raven; and, Beers et al. eds. (1999) The Merck Manual of Diagnosis and Therapy. 17th ed., Merck Sharp & Dohme Research Laboratories, Rahway, N.J.).

The extent of cerebral edema and mass effect can be determined by CT scans. For example, the volume of focal lesions can be measured. Mass lesions, either high-density or mixed-density abnormalities, will be evaluated by measuring the area of the abnormality as a region of interest, multiplying the area by the slice thickness, and summing these volumes for contiguous slices showing the same lesion. Each lesion will be measured three times, and the mean volume will be entered. This technique has been shown to be reliable (Garcia-Estrada et al. (1993) Brain Res 628(1-2): 271-8). Intracerebral lesions can be further characterized by location (frontal, temporal, parietal, occipital, basal ganglia, or any combination).

In addition to the neurological measurements discussed above, a partial therapeutic response can also be assayed through various functional and neuropsychological outcomes. Several standardized measures of neuropsychological and functional performance are known. For instance subjects may display an improvement in the Glasgow Outcome Scale (GOS)/Glasgow Outcome Scale Extender (GOSE) and/or in the Disability Rating Scale (DRS). The Glasgow Outcome Score is one of the most widely used measures of brain injury recovery in the world (Garcia-Estrada et al. (1999) Int J Dev Neurosci 17(2): p. 145-51). Patients are classified into one of five categories: death, persistent vegetative state, severe disability, moderate disability, and good recovery. It is easy to administer and score, and has a high degree of reliability and validity.

The Disability Rating Scale (DRS) offers more precision than the GOS for measuring outcomes of moderate brain injury (Goodman et al. (1996) J Neurochem 66(5): 1836-44). The DRS consists of an eight-item rating of arousal and awareness, daily living activities, physical dependence, and employability (Vedder et al. (1999) J Neurochem 72(6): 2531-8). Inter-rater reliability for the entire DRS is high (0.97 to 0.98).

The Functional Independence Measure (FIM) can be used to assess physical and cognitive disability. It contains 18 items in the following domains: self-care, sphincter control, mobility, locomotion, communication, and social cognition (Baulieu (1997) Mult Scler 3(2):105-12). The FIM has demonstrated reliability and validity as an outcome measure following moderate and severe TBI (Jung-Testas et al. (1994) J Steroid Biochem Mol Biol 48(1):145-54).

The Sickness Impact Profile is one method for measuring self-perceived health status (Schumacher et al. (1995) Ciba Found Symp 191: p. 90-112 and Koenig et al. (1995) Science 268(5216):1500-3). It consists of 136 questions divided into 12 categories: sleep and rest, eating, work, home management, recreation and pastimes, ambulation, mobility, body care and movement, social interaction, alertness, behavior, emotional behavior, and communication. It has been widely used across a variety of diseases and injuries, including head injury (Thomas et al. (1999) Spine 24:2134-8). Baseline SIP scores will reflect pre-injury health status, while follow-up scores will examine post-injury functioning.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Methods for TBI Studies

Animal Handling

Rodent animal models are suitable for use to determine the dose, delivery system and timing of the application of TSE cells, including AMP cells, and/or ACCS. Male Sprague-Dawley rats weighing 250 to 300 g are typically used for the experiments. All procedures are approved by the Institutional Research Animal Care and Use Committee. Research is conducted in compliance with the Animal Welfare Act, Guide for the Care and Use of Laboratory Animals (National Research Council) and other federal statutes and regulations relating to animals and experiments involving animals. Animals are maintained in a facility accredited by the Association for Assessment and Accreditation of Laboratory Animal Care International. All surgical procedures are performed on rats anesthetized with 5% isoflurane for induction and 2% isoflurane in oxygen for maintenance or with intraperitoneal injections of Ketamine 1 gm+Xylazine 140 mg+Acepromazine20 mg IM 0.1 ml/125 gm as needed. No neuromuscular blockers are needed. Supplemental isoflurane 1%-2% free breathe $O_2$ administered by face mask. Canines are anesthetized by: Sedation: Ketamine I. M. 10 mg/kg with Xylazine 2.5 mg/kg; Isoflurane 5% by mask until relaxed for ET intubation; ET ventilation 2% isoflurane and 70% $O_2$. Goats or pigs are anesthetized by WPAFB AFRL/PHPA according to standard anesthetic techniques. For sacrifice of animals: All animals will be euthanized according to standards of AAALAC and the American Veterinary Association.

Animal Models for TBI

Penetrating Traumatic Brain Injury (PBBI): A multi-port probe with a balloon fastened over the probe will be inserted though a small trephine in the skull into the right hemisphere of the brain to produce cavitation damage to the unilateral frontal cortex and striatum to mimic the passage and ballistic force of a high-velocity missile, e. g. a bullet or fragment, through brain tissue Williams A J, et al, (2006) Neurosci Letters 408: 183-188. The apparatus of this model consists of a penetrating probe, a stereotaxic frame equipped with a specially designed probe holder and an HPD-1700 Variable Pressure Waveform Generator (Dragonfly Inc., W.Va.). The penetrating probe is made of a 20G stainless steel tube with perforations along one end that was sealed by a piece of elastic tubing (1 cm). The perforations of the probe are arranged in a pattern such that an air pulse delivered from the HPD-1700 Generator can inflate the elastic tubing into an elliptical shaped balloon. The probe is secured on the probe holder at an angle of 50 degrees from the vertical axis and 25 degrees counter clockwise from the midline with the un-perforated end attached to the HPD-1700 Generator.

To induce frontal PBBI, the head of the anesthetized rat is secured in the stereotaxic frame. The scalp is incised along the midline and a cranial window (1 cm in diameter trephine) is made on the skull (+4.5 mm AP, +2 mm ML to bregma) to expose the right frontal pole. The penetrating probe is then manually advanced through the cranial window along the axis described above, penetrating into the right frontal hemisphere to a distance of 1.2 cm from the surface of the brain. Once it is in place, the HPD-1700 Generator is activated via a falling pendulum strike to an air cylinder to deliver a rapid air pulse to inflate and deflate the elastic tubing on the probe into an elliptically shaped air balloon. The ballistic force of the balloon creates a temporary cavity in the brain which mimics the shock wave of a revolving bullet through the brain tissue. The probe is then retracted from the brain, the cranial opening is sealed with sterile bone wax, and the incision is closed with 3-0 silk suture followed by the administration of a topical antibiotic. By precisely controlling the air pressure delivered by the HPD-1700 Generator, the air balloon on the probe can be inflated to a size equal to 10% of the total rat brain volume, resulting in severe traumatic brain injury. Previous studies have shown realistic direct and secondary injury effects similar to penetrating TBI in humans (see McHale M K, et al, (2005) Tissue Eng 11:1768-1779).

Blunt Traumatic Brain Injury (Blunt TBI)

Blunt TBI will be delivered by a captured-bolt mechanism (MyNeuroLab.com—Blackmark, Stereotaxic Impactor). Each animal is placed in a directing framework with the device set to deliver the appropriate energy to an area on the skull 8 mm behind the bregma, 5 mm lateral to the midline. After the blunt trauma is conveyed to the rat brain, the device is removed from the frame. A delivery methodology is placed into each animal, fixed in place and imaging is done with specialized CT Scans and/or MRI of the brain.

Blast Traumatic Brain Injury (Blast TBI)

Blast TBI is delivered by an air blast gun/shock tube mechanism specifically designed to deliver a consistent blast TBI (standardized blast curve of overpressure, vacuum, duration of positive phase and negative phase, associated injuries, etc) to the brain of the rat at levels equivalent to those of the Blunt TBI model. Each animal is placed in a directing framework with the air blast device set to release an appropriate blast pressure curve to a 1 cm area on the skull 8 mm behind the bregma, 5 mm lateral to the midline without causing a skull fracture. After the blast trauma is delivered to the rat brain, the device is removed from the frame. A delivery methodology will be placed into each animal, fixed in place and imaging done with specialized CT Scan, MM, and/or DTI of the brain.

Functional Testing for Rats Following TBI

Rota Rod Test

A Rota rod apparatus (Columbus Instruments, Columbus, Ohio) is used to measure motor coordination and balance of the animal. Prior to procedures/operations, rats are trained on the Rota rod at a constant speed (16 rpm) until the rat is able to remain on the machine for a minimum of 60 seconds. Following PBBI (or Blunt TBI or Blast TBI) and AMP cell or ACCS treatment, rats are tested on the Rota rod performance on Day 3, 7, 14, 21, and 28 (or longer if necessary). On testing days, each rat receives two trials at each of the two constant speed levels (i.e. 20 and 25 rpm) and two trials of an accelerating speed (4-40 rpm within 2 min). The latency to fall off the Rota rod for each trial and the time on the Rota Rod is recorded and used in subsequent analysis.

Novel Object Recognition (NOR) Test: Rats have an intrinsic nature to explore a novel environment. The NOR task utilizes the rat's "curiosity" to measure its ability to discriminate an "old" familiar object from a novel object based on its memory of the "old" object (Ennaceur, A. and Delacour, J., Behav Brain Res. 1988 Nov. 1; 31(1):47-59). On Day 7, 14, 21, and 28, rats are placed in a plastic circular container (20 inches diameter×17 inches high) which contains two identical objects (12 inch apart) and allowed to explore for 5 min and then returned to their home cage. Three (3) hours later, one of the objects is replaced by a novel object distinctively different from the other object and the rat is placed in the container again for 5 min to explore both objects. The exploration time of the animal in both sessions is recorded by a video camera for analysis. A discrimination index (DI) is calculated as: [(Time spent exploring new object)−(Time spent exploring old object)]/[(Time spent exploring new object)+(Time spent exploring old object)]. The higher DI gives a better indication that the rat discriminates two objects based on memory of the old object.

Labeling AMP Cells with PKH26

To distinguish AMP cells in vitro or in vivo, PKH26 (Sigma PKH26-GL) is used for AMP labeling. PKH26 is a red lipophilic fluorescence dye that can be irreversibly incorporated into lipid cell membrane. The stain provides stable, intense, and accurate fluorescent labeling of cells and has been used to label various cell types in vitro prior to transplantation for recognition of grafted cells in the host tissue by a florescence microscope. AMP cells are pre-labeled with PKH26 for identification either in culture or in transplantation studies. Before labeling, the AMP cells are removed from the culture flask by trypsin, spun at 400 g for 5 minutes into a loose pellet and resuspended in Sigma Diluent C at $2\times10^7$ after supernatant removal. $16\times10^6$ M PKH26 will be prepared in Sigma Diluent C. The AMP cells are rapidly added into the PKH26 solution and mixed immediately to insure uniform labeling. The mixture is incubated at 25° C. for 5 minutes by periodically agitating. The staining is stopped by adding and equal volume of 1% BSA solution. The BSA-stopped sample is diluted with an equal volume of medium and centrifuged at 400 g for 5 minutes to remove cells from staining dye. The labeled AMP cells are washed once with 10 ml medium. In a pilot study, PKH26 labeled AMP cells can be viewed clearly under fluorescent microscope with rhodomine filter.

Isolating Axons with Campenot or Microfluidic Chambers

To prepare the Campenot system, twenty parallel scratches 200 µm apart are made on a poly-D-lysine coated plate with a rake of twenty cemented insect pins. Neurites growth is guided along the 200 µm-wide tracks between the scratches because they tend not to cross the scratches. To assemble the system, the scratched region is first coated with growth medium. Then a Tyler Campenot divider (Tyler Research Co, CAMP3), which serves to partition the petri dish into three chambers, is sealed to the dish with silicone grease previously applied to the entire lower surface of the divider through a blunted 22-gauge hypodermic needle. The grease is loaded into a syringe and autoclaved before application. The divider is seated so that the scratches crossed the floor of a narrow central chamber (1×5 mm) at right angles to its long dimension and entered into the chambers flanking it at the left and right. The coating of growth medium in the scratched region prevents the silicone grease from adhering there, but the grease presses against the surface firmly enough to prevent significant flow of medium between the central and side chambers. The primary neurons are plated in the two side chambers and their neurites grow towards the middle chambers. The microfluidic culture platform will be purchased from University of California in Irvine and the culture performed based on the manufacture's protocol.

Example 1: Preparation of AMP Cell Compositions

Recovery of AMP Cells

AMP cells were dissociated from starting amniotic membrane using the dissociation agents PXXIII, and trypsin. The average weight range of an amnion was 18-27 g. The number of cells recovered per g of amnion was about $10\text{-}15\times10^6$ for dissociation with PXXIII and $5\text{-}8\times10^6$ for dissociation with trypsin.

Culture Conditions

The primary AMP cells were cultured for 5 passages in the following media: Stemline II+10% FBS, Stemline II+10% plasbumin (pb), Ultraculture+10% plasbumin (pb), and DMEM+10% FBS. Each culture condition was tested using 15 million cells/g amnion, 10 million cells/g amnion, and 5 million cells/g amnion, depending on the enzyme used for recovery of the primary cells. For instance, using PXXIII, 15 million cells/g amnion were obtained, while using trypsin, 10 million cells/g amnion were obtained, while other enzymes resulted in even lesser recovery (5 million cells/g amnion).

Passaging

Cells were passaged 5 times as follows: The cells were grown attached to a culture flask (on tissue culture treated plastic). The cells were left to divide and grow. The cells were removed from the plastic using Tryple™ (Invitrogen), a trypsin-like product that is animal-free GMP grade. Once unattached, the cells were centrifuged, and the cell pellet removed and resuspended in the culture medium with protein and additives (10 ng/ml EGF) and replated back onto fresh flasks. Cells were grown in a humidified atmosphere at 37° C. and 5% $CO_2$.

The results indicate that the use of either Stemline or Ultraculture with added plasbumin (pb) or albumin, the primary cultures are expanded to a level that is at least 4 fold and as much as 10 fold higher than is obtained using previous methodology (DMEM with fetal bovine serum). Even the use of plasbumin (pb) in the basal media DMEM resulted in an expanded AMP cell composition, having a 3-fold increase in multipotent cells as compared to the previous method of using DMEM with fetal bovine serum. Details on these results are contained in US Publication No. 2006-0222634-A1, which is incorporated herein by reference.

Another significant result observed was that cells grown in medium containing plasbumin displayed a spheroidal phenotype after passaging. When the AMP cells were removed from the tissue culture surface with the digestive enzyme and replated, AMP cells formed small clusters of cells that were not firmly adhered to the culture surface. Some of the clusters of cells were completely in suspension. These AMP cell clusters proliferated until up to 200 cells were present in the clusters. After a period of 1-5 days, the clusters of cells reattached and flattened out to form an adherent monolayer. This clustering phenotype was observed at each passage. Further studies indicated that such clustering occurs in the following media containing either recombinant human albumin, plasbumin, or plasmanate: OptiPRO SFM, VP-SFM, Iscove's MDM, HPGM, UltraMDCK, Stemline II and Stemline I, DMEM, and DMEM:F12, but not in Advanced DMEM, Knockout DMEM, 293 SFM II, Pro 293 S-CDM, Pro 293A-CDM or UltracultureVP-SFM.

Example 2: Generation of ACCS

The AMP cells of the invention can be used to generate ACCS. The AMP cells were isolated as described herein and $1\times10^6$ cells/mL were seeded into T75 flasks containing 10 ml culture medium. The cells were cultured until confluent, the medium was changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention (see above). It is also contemplated by the instant invention that the ACCS be cryopreserved following collection. It is also contemplated that the ACCS be lyophilized or formulated for sustained-release.

Example 3: Detection of Growth Factors and Cytokines Important in Treating CNS Disorders To determine which growth factors and/or cytokines important in treating CNS disorders may be secreted by the AMP cells of the present invention, ACCS was isolated from cell cultures that were seeded onto tissue culture treated flasks at a density of ~40,000 cells per $cm^2$. Cells were cultured in serum-free medium supplemented with 10 ng/ml of EGF. Culture media was exchanged every 2 days during the growth period. After cells reached near confluency (~1-2 wk after isolation), fresh media was applied and ACCS was collected after three days and stored at −80° C. for subsequent analysis. ACCS was analyzed for secreted factor content via antibody arrays, ELISA, multiplex assays and Mass spectrometry. Results are as follows:

NGF—NGF has long been studied for its neurotrophic and neuroprotective effects. For example, NGF is known to promote the survival of sympathetic neurons (Pierchala, B. A., et al., J Biol Chem 279(27):27986-27993, 2004; Godfrey, E. W. and Shooter, E. M., J Neurosci, 6(9):2543-2550, 1986) and to protect cholinergic neurons against excitotoxic injury (Perez-Navarro, E., et al. Eur J Neurosci 6(5):706-711, 1994).

FGF-4—In vitro, FGF-4 generates large proliferative neurospheres that have multipotent differentiation ability (Kosaka, N., et al, FASEB J, 20(9):1484-5, 2006).

GDNF—GDNF has long been studied as a neurotrophic factor. For example, GDNF and has been shown to be neuroprotective for dopamine neurons against 6-OHDA treatment in rats (Fox, C. M., et al., Brain Res 896(1-2):56-63, 2001; Cass, W. A., et al, Ann NY Acad Sci 1074:272-81, 2006); Choi-Lundberg, D. L., et al, Exp Neurol 154(2):261-75, 1998). This is of particular importance in the context of Parkinson's disease.

IGF-II—IGF-II protects and rescues rat hippocampal neurons against β-amyloid- and human amylin-induced toxicity, although it is not as potent as IGF-I; IGF-I and IGF-II protect cultured rat hippocampal and septal neurons against calcium-mediated hypoglycemic damage (Doré, S., et al, PNAS USA 94(9):4772-4777, 1997; Cheng, B., and Mattson, M. P., J Neurosci 12(4):1558-66, 1992).

TIMP-1 and TIMP-2—MMP9 causes neuron death in neurotoxicity models and MMP inhibitors (i.e. minocycline) can prevent such damage. (Yong, V. W., et al, Neurology 68:S32-S37, 2007). TIMPs are natural inhibitors of MMPs, so their presence may serve a neuroprotective function.

BDNF—BDNF has long been studied for its neurotrophic and neuroprotective effects. In the brain BDNF has a trophic action on retinal (Ikeda, K., et al, Invest Ophthalmol Vis Sci 40:2130-2140, 1999; Menna, e., et al, Mol Cell Neurosci 24(4):972-83, 2003), cholinergic (Widmer, H. R., et al, Neuroreport 4(4):363-6, 1993; Morse, J. K., et al, J Neurosci 13(10:4146-56, 1993), and dopaminergic neurons (Spenger, C., et al, Exp Neurol 133(1):50-63, 1995; Frim, D. M., et al, PNAS 91:5104-5108, 1994), and in the peripheral nervous system it acts on both motor (Kishino, A. and Nakayama, C., Brain Res 964(1):56-66, 2003; Tsuzaka, K., et al, Muscle & Nerve, 24(4):474-480, 2001) and sensory (Wang, H., et al, Eur J Neurosci 24(9):2444-2452, 2006; Acheson, A., et al, Nature 374:450-453, 2002; Song, X-Y., et al, PLoS ONE 3(3):e1707, 2008) neurons.

CNTF—CNTF has long been studied for its neurotrophic and neuroprotective effects (Ping, L., et al, Chinese Sci Bulletin 51(1):48-53, 2006). Richardson, P. M. (Pharmacolo Ther 1994 63(2):187-98) reviewed the CNTF literature and reported that in vitro CNTF supports survival of all classes of peripheral nervous system neurons plus many CNS neurons, induces neurite outgrowth, promotes a cholinergic phenotype in sympathetic neurons and arrests division of neuronal precursor cells. In vivo, CNTF rescues several types of neurons from axotomy-induced death.

EGF—Angenieux, B., et al, Stem Cells 24(3):696-706, 2005, report that epidermal growth factor is a neuronal differentiation factor for retinal stem cells. Casper, D., et al, J of Neurosci Res 30(2):372-381, 2004, report that EGF enhances the survival of dopamine neurons in rat embryonic mesencephalic primary cell culture. Morrison, R. S., et al, Science 238(4823):72-75, 1087, report trophic stimulation of cultured neurons from neonatal rat brain by EGF. Casper, D. and Blum, M., J Neurochem 65(3):1016-1026, 1995, report that EGF and bFGF protect dopaminergic neurons from glutamate toxicity in culture.

EGF-R—EGF-R is involved in myelination/remyelination of neurons in mice (Aguirre, A., et al, Nat Neurosci 10(8):990-1002, 2007).

bFGF—Basic FGF attenuates amyloid β-peptide-induced oxidative stress, mitochondrial dysfunction, and impairment of Na+/K+-ATPase activity in cultured hippocampal neurons (Mark, R. J., et al, Brain Res 756, Issue 1-2:205-214, 1997).

GITR Ligand, GITR

GITRL enhances NGF-promoted neurite outgrowth from neonatal mouse sympathetic neurons (O'Keefe, G W, et al, Nature Neurosci 11:135-142, 2007).

M-CSF—M-CSF protects spiral ganglion neurons following auditory nerve injury in a rat (Yagihashi, A., et al. Exp Neurol 192, Issue 1:167-177, 2005).

GRO and GROα—Proliferation/migration of rat oligodendrocyte progenitors (Filipovic, R. et al, Dev Neurosci Vol 25, No. 2-4, 2003).

HGF—HGF attenuates gliosis and motoneuronal degeneration in the brainstem motor nuclei of a transgenic mouse model of ALS (Kadoyama, K., at al, Neurosci Res 59(4): 446-56, 2007. Intrathecal delivery of HGF from ALS onset suppresses disease progression in a rat ALS model (Ishigaki, A., et al, Neuropathol Exp Neurol 66(11):1037-44, 2007. HGF protects cultured neurons against hypoxia/reoxygenation induced cell injury via ERK1/2 and PI-3K/Akt pathways (He, F., et al, Colloids Surf B Biointerfaces 61(2):290-7, 2008).

Thymosin β4

Thymosin β4 has been shown to be involved in the development of neurons, especially sensory neurons, in developing X. laevis (Yamamoto, M., et al, Brain Res Dev 79(2):177-185, 1994); Thymosin β4 has been shown to provide neuroprotection in experimental models of excitotoxicity (Popli, P., et al, Ann NY Acad Sci 1112(1):219-224, 2007); Thymosin β4 has been shown to have neuroprotective and neurotrophic effects via cytostolic actin-remodeling activity and extracellular antiapoptotic activity (Sun, W. and Kim, H., Ann NY Acad Sci 1112(1):210-218, 2007).

ICAM-2—ICAM-2 has been postulated to have a role in angiogenesis as a homophilic cell adhesion molecule (Vestweber, D., Blood 105(5):1510-1511, 2005).

Example 4: Treatment with AMP Cells as a Neuroprotective Therapy for Traumatic Brain Injury AMP cells were tested in a rat model of Penetrating Ballistic-like Brain Injury (PBBI) (Williams, A. J., 2005, "Characterization of a New Rat Model of Penetrating Ballistic Brain Injury", J Neurotrauma 22; 3:313-331) to test their neuroprotective potential. The AMP cells were labeled with fluorescent dye PKH26 (as described above) after two passages, suspended in conditioned medium, and injected in rats ($2\times10^6$ cells/50 μl/rat) immediately following right frontal PBBI or sham PBBI surgery by ipsilateral i.c.v. administration ($2\times10^6$ cells/50 μl/rat). PBBI controls received i.c.v. injection of PBS, control medium, or conditioned medium (50 μl/rat). After 3 weeks' survival, severe necrotic injury developed along the PBBI track and no significant difference in injury volume has been observed in all treatment groups. In non-AMP cell treated PBBI rats, silver stained axonal degeneration was prominent along the corpus callosum and in the ipsilateral thalamus. In contrast, the AMP cell treatment significantly attenuated axonal degeneration in both of these areas. Interestingly, PKH26 labeled AMP cells were detected only in the subventricular zone (SVZ) and the corpus callosum (parallel with the axonal degeneration), but not in the thalamus, and none of these labeled AMP cells appeared to express neural differentiation evidenced by the lack of double labeling with GFAP and MAP-2 immunostaining. No migration and neuronal differentiation of AMP cells was detected in the non-injury control group although cells did survive at the injection site.

These results indicate that AMP cell migration is specifically induced by PBBI and requires SVZ homing, yet the neuroprotective effect of i.c.v. treatment of AMP cells is not limited to the area where migrated AMP cells are present, suggesting that the attenuation of the secondary brain injury following PBBI is likely to be mediated by mechanisms other than cell replacement, possibly through sustained secretion of neurotrophic factors which AMP cells are known to secrete in physiological levels and in a physiologically relevant temporal fashion.

One of skill will appreciate that TSE cells, including AMP cells, can be used to treat brain injury immediately upon isolation, at p0 or after passaging.

Example 5: Treatment with AMP Cells in Combination with Collagen-Based Matrix as a Neuroprotective Therapy for Traumatic Brain Injury One of the histopathological consequences of a penetrating ballistic-like brain injury (PBBI) is the permanent brain cavitation that becomes unsalvageable once it develops. In Example 4 above, AMP cells suspended in conditioned media injected directly in the injury tract/brain cavity failed to survive. This was likely due to the absence of a supportive matrix at the localized wound site. Thus, AMP cells were seeded in a collagen-based scaffold prior to injection to investigate AMP cell survival and the neuroprotective support they may provide in the rat PBBI model.

AMP cells, labeled with the fluorescent dye PKH26, were either suspended in conditioned medium or a liquefied collagen matrix ($2\times106$ cells/150 μL/rat) that solidifies at 37° C. Control rats received only the liquefied collagen matrix (150 μL/rat). Injections were delivered along the PBBI tract (from the frontal cortex through the dorsal striatum) immediately after injury (n=5/grp). Serial sections of the injury site and surrounding areas of the brain were prepared two weeks post-injury.

Results—Consistent with previous results, AMP cells suspended in the conditioned medium failed to survive at the injury site. In contrast, AMP cells seeded in the collagen-based scaffold survived and were present in the injury cavity. Labeled AMP cells were also found in the subventricular zone of the lateral ventricle and in the corpus callosum. Importantly, the AMP cell/collagen treatment significantly attenuated PBBI-induced axonal degeneration (as determined by silver staining) in the corpus callosum and ipsilateral thalamus, compared to controls. In conclusion, a solidified collagen-based scaffold provided a supportive matrix for AMP cell survival, migration, and neuroprotection when injected along the PBBI tract immediately after injury.

Example 6: Use of AMP Cells to Treat Spinal Cord Injury in NOD SCID Mice

Transplantation of AMP cells—Nine days after contusion injury (see, for example, Constantini, S., and Young, W.

(1994), J. Neurosurg. 80, 97-111; Anderson, A. J., et al., Journal of Neurotrauma 21 (12), 1831-1846 for animal models), AMP cells (75,000 cells/μL) were transplanted and vehicle was injected (controls) into two different sites, the injury epicenter (1 μL) or the adjacent nervous tissue parenchyma (250 nL).

Analysis—Open field locomotor testing is the standard of the spinal cord injury field, because it is the only task which allows the investigator to evaluate a full spectrum of potential recovery, from complete paralysis (a 0 on the BBB or BMS) to fully normal locomotion (a 21 on the BBB, and a 9 on the BMS). However, these are nonlinear (ordinal) scales. It is not a direct comparison of the number of points of change that is relevant, but rather what these points represent in terms of specifically recovered locomotor function. In these tasks, animals move freely in a circular area for a four minute testing period while two investigators blinded to experimental group observe and rank the animals based on specific criteria on each testing scale. In the case of the range of recovery for the animals in this pilot, the key criterion scored by the investigators involves the ability to achieve consistent stepping and complete coordinated "passes". Each unbroken series of movements across the arena greater than three body lengths is defined as a pass. Normal animals make one hindlimb step for each forelimb step; missed steps decrease the score an animal achieves on the scale.

Results—The results suggest an improvement in spinal cord epicenter AMP cell-transplanted animals versus control animals, which is significant at some time points and exhibits a trend at others. The improvement observed for the epicenter transplanted animals reflects the gain of coordinated locomotion. Using this limited experimental design, it was not possible to determine whether transplantation into the adjacent parenchyma could result in improved locomotor activity. In addition, histological analyses need to be done to determine if there is evidence of differentiation and/or regeneration.

Example 7: Therapeutic Potential of TSE Cells and/or Conditioned Media Derived Therefrom, Including AMP Cells and ACCS, in Animal Models of Nervous System Disorders Alzheimer's Disease—Wenk, G. L. (Behav Brain Res 1993 57(2):117-22) describe a model of Alzheimer's disease which is based upon the assumption that the destruction of basal forebrain cholinergic neurons by injection of a neurotoxin, such as ibotenic acid, is sufficient to reproduce the cognitive impairments associated with Alzheimer's disease. TSE cells, including AMP cells and/or ACCS, are tested in this model of Alzheimer's disease.

Parkinson's disease—Arai, N., et al. (Brain Res 1990 515(1-2):57-63) describe an animal model for parkinsonism in which C57 black mice are treated with MPTP. The authors conclude that this model is a suitable model for studying Parkinson's disease. TSE cells, including AMP cells and/or ACCS, are tested in this model of Parkinson's disease.

Huntington's disease—Reddy, P. H., et al., (Nat Genet 1998 20(2):198-202) describe an experimental model for Huntington's disease in which transgenic mice were created that exhibited widespread expression of the full-length human Huntington's disease cDNA with either 16, 48 or 89 CAG repeats. The mice with 48 or 89 CAG repeats manifested progressive behavioral and motor dysfunction with neuron loss and gliosis in the striatum, cerebral cortex, thalamus and hippocampus. The authors conclude that this model is a clinically relevant model for Huntington's disease pathogenesis. TSE cells, including AMP cells and/or ACCS, are tested in this model of Huntington's disease.

Amyotrophic Lateral Sclerosis—Pioro, E. P. and Mitsumoto, H. (Clin Neurosci 1995-1996 3(6):375-85) describe four animal models of ALS. TSE cells, including AMP cells and/or ACCS, are tested in these models of ALS.

Spinal muscular atrophy—Monani, U. R., et al., Hum Mol Genet 2000 9(16):2451-2457) review animal models of spinal muscular atrophy. TSE cells, including AMP cells and/or ACCS, are tested in these models of spinal muscular atrophy disease.

Multiple sclerosis—Peiris, M., et al., (J Neurosci Methods 2007 Mar. 30 epub) describe an animal model of experimental autoimmune encephalomyelitis (EAE) in C57BL/6 mice useful for the characterization of intervention therapies to treat Multiple sclerosis. TSE cells, including AMP cells and/or ACCS, are tested in this model of Multiple sclerosis.

Peripheral neuropathy—Fricker, et al, (Neurodegen Dis 2008, 5:72-108) provide an extensive review of experimental peripheral neuropathy, including a comprehensive outline of numerous animal models useful in studying all types of peripheral neuropathy. For example, animal models for inherited (HNPP, CMT1A, CMT1B, DSS, CMT1X, CMT4B1), infectious (Leprosy, HIV), immune (GBS), diabetic (Type I, Type II), injury (transient nerve crush, chronic constriction injury, partial nerve ligation, spinal nerve ligation, spared nerve injury), and chemotherapy (i.e. cisplatin)-induced neuropathies are provided. TSE cells, including AMP cells and/or ACCS, are tested in these models of peripheral neuropathy.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for treating a closed-head traumatic brain injury in a patient in need thereof comprising the step of administering to the patient a therapeutically effective amount of a composition selected from the group consisting of Amnion-derived Cellular Cytokine Solution (ACCS) and Amnion-derived Multipotent Progenitor (AMP) cells.

2. The method of claim 1 wherein the ACCS is pooled ACCS.

3. The method of claim 1 wherein the closed-head traumatic brain injury is selected from the group consisting of Shaken Baby Syndrome, blast injury, blunt trauma, concussion, and concussion syndrome.

4. A method for relieving or ameliorating neurodegeneration in the brain caused by a closed-head traumatic brain injury in a patient in need thereof comprising the step of administering to the patient a therapeutically effective amount of a composition selected from the group consisting of ACCS or AMP cells.

5. The method of claim 4 wherein the ACCS is pooled ACCS.

6. The method of claim 4 wherein the closed-head traumatic brain injury is selected from the group consisting of Shaken Baby Syndrome, blast injury, blunt trauma, concussion, and concussion syndrome.

* * * * *